United States Patent [19]

Okabayashi et al.

[11] Patent Number: 5,756,313

[45] Date of Patent: May 26, 1998

[54] ALBUMIN GENE-CONTAINING PLASMID, TRANSFORMANT CARRYING SAME, PRODUCTION OF SUCH TRANSFORMANT AND PRODUCTION OF ALBUMIN

[75] Inventors: Ken Okabayashi; Hideyuki Oi; Kazumoto Hirabayashi; Masami Miura; Miho Shimizu; Haruhide Kawabe, all of Osaka, Japan

[73] Assignee: The Green Cross Corporation, Osaka, Japan

[21] Appl. No.: 138,384

[22] Filed: Oct. 20, 1993

Related U.S. Application Data

[63] Continuation of Ser. No. 985,230, Dec. 2, 1992, abandoned, which is a continuation of Ser. No. 526,917, May 22, 1990, abandoned.

[30] Foreign Application Priority Data

| May 22, 1989 | [JP] | Japan | 1-129927 |
| Sep. 8, 1989 | [JP] | Japan | 1-234481 |

[51] Int. Cl.⁶ ............ C12N 15/00; C12N 15/14; C12N 1/19
[52] U.S. Cl. .................. 435/69.9; 435/255.2; 435/255.5
[58] Field of Search .................. 435/69.1, 69.6, 435/69.7–69.9, 255.1–255.2, 255.5, 320.1, 172.3

[56] References Cited

U.S. PATENT DOCUMENTS

| 4,745,057 | 5/1988 | Beckage et al. | 435/69.1 |
| 4,876,197 | 10/1989 | Burke et al. | 435/172.3 |
| 4,880,741 | 11/1989 | Davidow et al. | 435/172.3 |
| 4,882,279 | 11/1989 | Cregg | 435/172.3 |
| 4,937,189 | 6/1990 | Davidow et al. | 435/69.1 |
| 4,937,193 | 6/1990 | Hinchliffe | 435/172.3 |
| 4,959,316 | 9/1990 | Stanislas et al. | 435/172.3 |
| 5,102,789 | 4/1992 | Siegel et al. | 435/69.4 |
| 5,330,901 | 7/1994 | Prevatt et al. | 435/69.6 |
| 5,409,815 | 4/1995 | Nakagawa et al. | 435/69.1 |
| 5,422,267 | 6/1995 | Yocum et al. | 435/254.21 |
| 5,503,993 | 4/1996 | Hayasuke et al. | 435/69.8 |

FOREIGN PATENT DOCUMENTS

| 226752 | 7/1987 | European Pat. Off. |
| 0248637 | 12/1987 | European Pat. Off. |
| 251744 | 1/1988 | European Pat. Off. |
| 308381 | 3/1989 | European Pat. Off. |
| 319641 | 6/1989 | European Pat. Off. |
| 329127 | 8/1989 | European Pat. Off. |
| 344459 | 12/1989 | European Pat. Off. |
| 2563533 | 10/1985 | France |
| 88/03169 | 5/1988 | WIPO |

OTHER PUBLICATIONS

Rose, M. et al., *J. Mol. Biol.*, 170: 883–904, 1983.
Bitter, G.A. et al., *Methods In Enzymology*, 153: 516–543.
Orr-Weaver, T. et al., *Methods In Enzymology*, 101: 228–245, 1983.
Lopes, T.S. et al., *Gene*, 79 (2): 199–206, 1989.

*Primary Examiner*—Marianne P. Allen
*Attorney, Agent, or Firm*—Sughrue,Mion,Zinn,Macpeak & Seas, PLLC

[57] ABSTRACT

A plasmid for a yeast host, the plasmid comprising in sequence: (1) a yeast derived promoter, (2) an albumin-encoding region placed under control of the yeast-derived promoter, (3) a transcription terminator and (4) a sequence homologous to a part of the yeast host chromosomal sequence such that the plasmid is capable of being integrated into the yeast host cell chromosome and wherein the plasmid is incapable of autonomous replication in yeast cells; a yeast host transformed with the above plasmid; a method of producing a yeast transformant which comprises transforming a yeast host by integrating at least two different plasmids each having a sequence homologous to a part of the host yeast chromosomal sequence one at a time into the chromosome of the yeast host cell; and a method of producing albumin which comprises cultivating the above transformant and recovering the thus-produced albumin.

5 Claims, 31 Drawing Sheets

ALBUMIN GENE-CONTAINING PLASMID, TRANSFORMANT CARRYING SAME, PRODUCTION OF SUCH TRANSFORMANT AND PRODUCTION OF ALBUMIN

This is a Continuation of application Ser. No. 07/985,230 filed 2 Dec. 1992 now abandoned which is a continuation of application Ser. No. 07/526,917 filed 22 May 1990.

FIELD OF THE INVENTION

This invention relates to a plasmid to be used for the production of albumin by utilizing recombinant DNA techniques, to a yeast host transformed with said plasmid, to a method of producing the thus-transformed yeast cells, and to a method of producing albumin using said transformed yeast host.

BACKGROUND OF THE INVENTION

Albumin, in particular human serum albumin (hereinafter referred to as "HSA"), is a major plasma constituent protein. This protein is produced in the liver and serves, mainly in blood circulation, to maintain the osmotic pressure in the blood within a normal range.

It also functions as a carrier for various serum molecules.

HSA is administered in various clinical conditions. In shock or burn cases, for instance, frequent administration of HSA is generally required for regaining a normal level of blood volume to thereby improve trauma-associated symptoms. In some patients with hypoproteinemia or fetal erythroblastosis, therapeutic treatment with HSA is required as well.

Accordingly, the fundamental therapeutic significance of HSA administration lies in treating conditions in which there is a fluid loss from the blood vessel, for example conditions encountered upon surgical operation, shock, burn, or edema-inducing hypoproteinemia.

At the present time, HSA is produced mainly as a fractionation product from the blood collected from donors. This production method is disadvantageous in that it is uneconomical and in that the blood supply is difficult to procure. In certain instances, blood may contain undesirable substances, such as hepatitis virus. Therefore, it would be very helpful if an HSA substitute could be developed.

Meanwhile, the advent of recombinant DNA technology has already made it possible to produce a variety of useful polypeptides in microorganisms. A number of mammalian polypeptides, for example human growth hormone and interferons, are already in large-scale production using various microorganisms. This technology has also enabled production of various vaccines, hormones, enzymes and antibodies in microorganisms.

However, protein products derived from microorganisms, in particular *Escherichia coli*, are frequently found to be contaminated with endotoxins. These must be removed from the desired protein products.

It has been established that growth of mammalian cells is difficult to achieve on a scale large enough for low-cost and advantageous production of proteins which are secreted from the cells. One generation of mammalian cells is considerably long compared with one generation of microorganisms and therefore a long cultivation period is required for a sufficiently high cell concentration to be attained. Furtheremore, the maximum cell concentration attainable by cultivation of mammalian cells is considerably lower than that generally obtainable in large-scale cultivation of microorganisms. In addition, cell line improvement is difficult as compared with that of microorganisms.

Since all eukaryotes have mechanisms for expression of genetic information, it is expected that eukaryotic genes might be expressed more efficiently in eukaryotic hosts than in prokaryotes, such as *Escherichia coli*. Among eukaryotes suited for use, yeasts can be handled most easily. It is known that the secretory pathway in yeasts resembles that in higher animal cells and further that, in yeast cells, proteins can be processed in such a manner that the signal sequence (non-charged N-terminal portion of proteins; generally cleaved during transportation for secretion) is cleaved. Proteins which enter and pass through the secretory pathway in eukaryotic hosts presumably have more three-dimensional structure as compared with proteins synthesized in the cytoplasm. It is interesting that prokaryotes, such as *Escherichia coli*, seem to have no large-sized proteins with a three-dimensional structure.

Further, the glycosylation system in eukaryotes is associated with the secretory system. The basic stage at which glycosylated proteins are derived is similar among all eukaryotes. Yeast cells can produce glycosylated proteins, unlike prokaryotes, such as *Escherichia coli*.

Since yeasts are microorganisms, it is easy to cultivate them. The number of yeast cells obtainable per unit volume of culture is considerably greater as compared with *Escherichia coli*. The behavior of yeasts in fermentation has been thoroughly understood and optimal conditions for large-scale fermentation have already been established for them. Furthermore, yeast cells are free of endotoxins.

It is therefore evident that it is advantageous, if successful, to produce albumin, particularly HSA, in yeasts using the well-developed industrial microbiology techniques and the recently developed recombinant DNA techniques.

Some methods are known for the production of HSA by utilizing the recombinant DNA technology with yeasts as host organisms (U.S. patent application Ser. No. 488,323 now abandoned or EP-A-123544, EP-A-248637 and EP-A-251744).

Where large-quantity production of HSA is intended, large-scale yeast cultivation is essential. In the current state of the art, when a transformant yeast is cultivated, the plasmid containing the desired gene is frequently lost from host cells during cultivation. For preventing growth of yeast which has lost the plasmid, it is necessary to provide a selective marker (e.g. nutrient requirement marker, drug resistance marker) in said plasmid. In that case, however, an amino acid or drug corresponding to the selective marker must be added to the medium. This means an increase in production cost.

SUMMARY OF THE INVENTION

Accordingly, it is an object of the invention to provide a plasmid for recombination in which the desired gene, namely the albumin gene, in particular the HSA gene, can be retained without application of any selection pressure, a transformant transformed with said plasmid, a method of producing such transformant and a novel method of producing albumin, in particular HSA.

The invention thus provides:

(1) A plasmid for a yeast host, the plasmid comprising in sequence: (1) a yeast-derived promoter, (2) an albumin-encoding region placed under control of the yeast-derived promoter, (3) a transcription terminator, and (4) a sequence homologous to a part of the yeast host chromosomal sequence such that the plasmid is capable of being integrated into the yeast host cell chromosome, and wherein the plasmid is incapable of autonomous replication in the yeast host cells;

(2) A yeast host transformed with the above plasmid;

(3) A method of producing a yeast transformant which comprises transforming a yeast host by integrating at least two different plasmids each having a sequence homologous to a part of the host yeast chromosomal sequence one at a time into the chromosome of the host yeast cell; and (4) A method of producing albumin which comprises cultivating a yeast host transformed with a plasmid for a yeast host, the plasmid comprising in sequence: (1) a yeast-derived promoter, (2) an albumin-encoding region placed under control of the yeast-derived promoter, (3) a transcription terminator, and (4) a sequence homologous to a part of the yeast host chromosomal sequence such that the plasmid is capable of being integrated (inserted) into the yeast host cell chromosome, and wherein the plasmid is incapable of autonomous replication in yeast cells and recovering the thus-produced albumin.

BRIEF DESCRIPTION OF THE DRAWING

In FIG. 1A to FIG. 10, ■ indicates promoter, ▦ signal sequence, ▨ the HSA structural gene, ▤ terminator, ▩ the sequence homologous to the corresponding region of the yeast chromosome, and →the direction of transcription.

DETAILED DESCRIPTION OF THE INVENTION

Figure 1A:
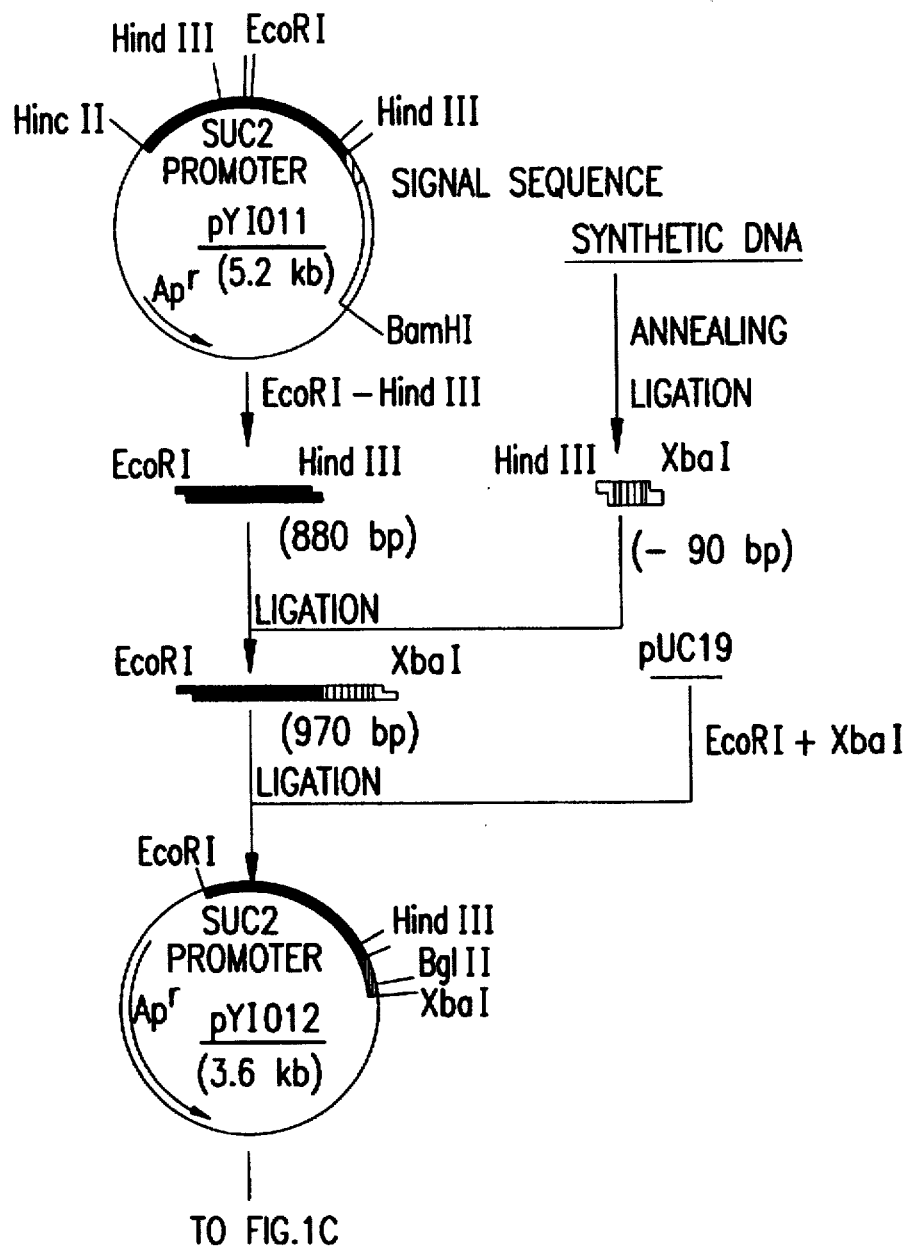
FIGS. 1A–1D show a process for constructing the plasmids pYI014 and pYI016.
Figure 1B:
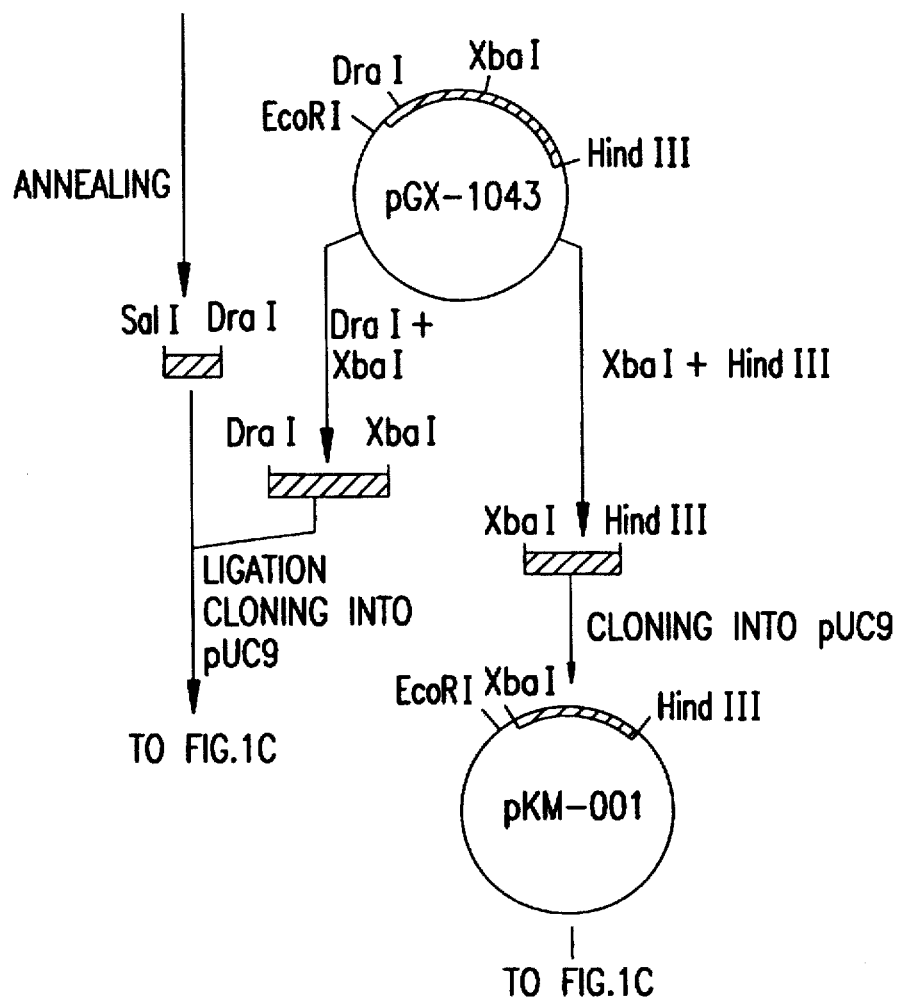
Figure 1C:
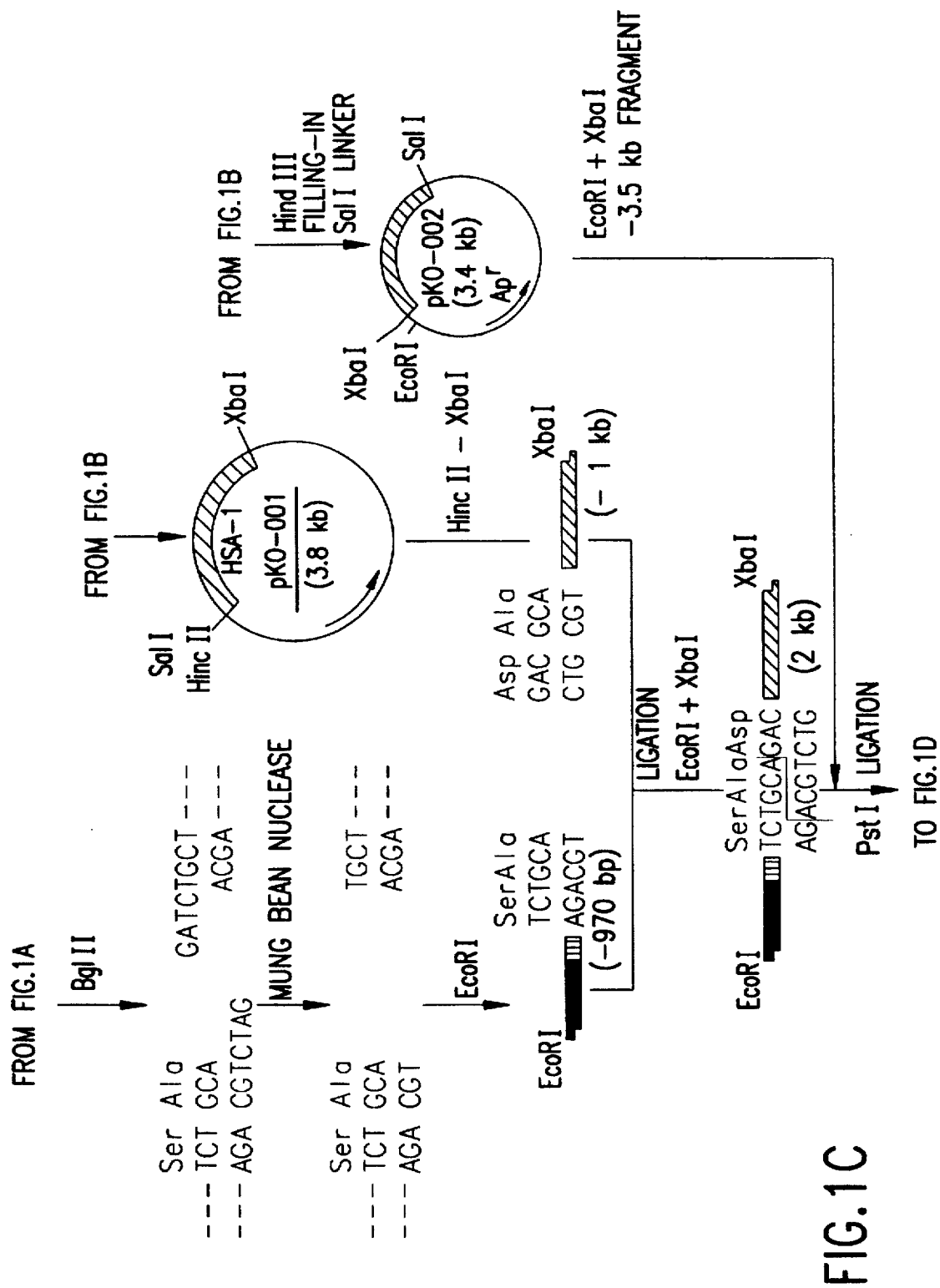
Figure 1D:
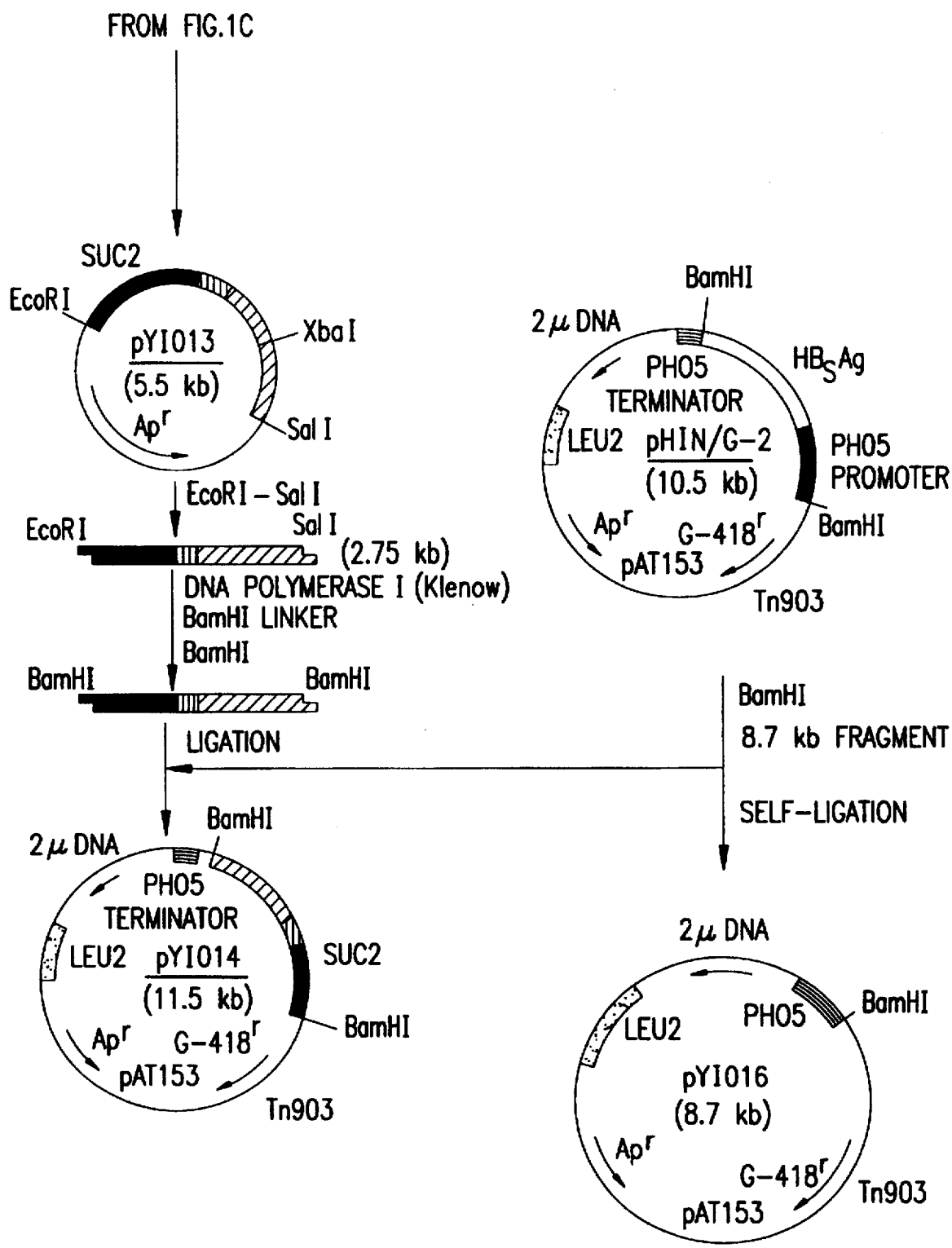

In the following, the invention is described in further detail with HSA as the central figure.

The plasmid according to the invention contains a homologous sequence comprising the DNA sequence of a part of a gene occurring in the host yeast chromosome (e.g., LEU2, HIS4, TRP1, URA3, ribosome DNA gene) and therefore can be stably integrated, either as such or in its linearized fragment form, into the host chromosome as a result of recombination. Thus, offspring cells can retain the transferred genetic material stably during proliferation even when no selection pressure is present.

For example, when the plasmid contains a sequence naturally occurring in a gene on the yeast chromosome together with the HSA gene, the plasmid can be stably integrated into the chromosome at the locus of the gene on the chromosome.

The sequence homologous to a part of a gene of the yeast host chromosome may be a sequence homologous to a whole gene or a part of a whole gene.

Particularly useful as the sequence homologous to a part of the host yeast chromosomal sequence are an amino acid or nucleic acid base (or precursor) synthesis gene, the ribosome DNA and the Ty element, among others. In particular, an amino acid or nucleic acid base synthesis gene can be used as a selective marker for transformants since when the yeast host is an amino acid- or nucleic acid-requiring strain, namely an amino acid or nucleic acid base synthesis gene-deficient strain, such amino acid or nucleic acid base synthesis gene serves as a gene for complementing the relevant mutation in the host. In this case, the auxotrophic host yeast becomes prototrophic. As the amino acid or nucleic acid base synthesis gene, there may be mentioned LEU2, HIS4, TRP1 and URA3, for instance.

Usable as the selective genetic marker to serve in yeast are amino acid or nucleic acid synthesis genes when the yeast host is an auxotroph, as mentioned above. When the host is an antibiotic-susceptible strain, the gene for the antibiotic resistancy can be used. As such gene, there may be mentioned genes providing resistance to such antibiotics as cycloheximide, G418, chloramphenicol, bleomycin and hygromycin. The plasmid of the present invention may have one or more selective genetic markers.

The albumin-encoding region that the plasmid according to the invention contains is particularly a DNA sequence identical or homologous to the sequence coding for human serum-derived albumin (HSA) and can be obtained, for example, from any human cell line capable of producing HSA. Such DNA may be a chromosomal DNA or a cDNA. The chromosomal DNA can be isolated from among a gene library containing an HSA gene, while the HSA cDNA can be prepared via the corresponding mRNA using an appropriate known method.

The promoter to be used in the practice of the invention is derived from the genome DNA of a yeast, preferably Saccharomyces cerevisiae (EP-A-206733 or U.S. patent application Ser. No. 745,524[).] It is preferable to use the promoter of a high expression yeast gene for the expression of HSA. Thus usable are the promoter of the TRP1 gene, ADHI or ADHII gene, acid phosphatase (PHO3 or PHO5) gene or cytochrome c gene, the galactose metabolic system promoter (GAL1, GAL10 or GAL7), the invertase promoter (SUC2), the promoter of a gene coding for an enzyme involved in glycolysis, e.g., the promoter of the enolase, glyceraldehyde-3-phosphate dehydrogenase (GAP-DH), 3-phosphoglycerate kinase (PGK), hexokinase, pyruvate decarboxylase, phosphofructokinase, glucose-6-phosphate isomerase, 3-phosphoglycerate mutase, pyruvate kinase, triphosphate isomerase, phosphoglucose isomerase or glucokinase gene or the like, and the promoter of the yeast mating pheromone gene coding for the a factor or α factor. Among these, preferable pomoters are the GAP-DH promoter, the PGK promoter and GAL1 promoter.

The plasmid according to the invention is incapable of autonomous replication in host yeasts. Thus, it is substantially free of any region for initiating autonomous replication in host yeasts, for example the 2 μm DNA replication origin or the ARS (autonomously replicating sequence).

In a preferred embodiment of the invention, a signal sequence is introduced into the plasmid structure. Usable as the signal sequence are yeast-derived signal sequences, such as the yeast invertase gene (SUC2 signal sequence), α factor gene, with the SUC2 signal sequence being preferred. The HSA signal sequence is a preferable one and a signal sequence specifically synthesized for secretory expression in yeasts (U.S. patent application Ser. Nos. 190,553 now abandoned and 311,556 now U.S. Pat. No. 5,409,815 corresponding to EP-A-319641 and EP-A-329127, respectively) can be preferably used as well.

As a result of the introduction of such a signal sequence, the HSA gene product, after expression of the gene, enters the secretory pathway and is transported to the periplasmic space. The protein can further be secreted, through the cell wall, into the medium. This results in a considerable increase in yield. Furthermore, since cell disruption is not required, the step of recovery can be simplified.

The plasmid according to the invention further contains an appropriate terminator for terminating transcription, for example the PH05 or GAP-DH terminator.

The plasmid may further contain an origin of replication from bacterial hosts, in particular *Escherichia coli*, as well as a selective genetic marker for *Escherichia coli* in addition to the promoter, HSA-encoding region, transcription terminator and region homologous to a part of the yeast host chromosomal sequence. The use of such an origin of replication from *Escherichia coli* and a selective marker for *Escherichia coli* to give a yeast hybrid vector has useful features. First, the hybrid vector DNA can be prepared in large amounts by growing *Escherichia coli* for replication of the DNA. Secondly, such a hybrid vector can be constructed readily by taking full advantage of *Escherichia coli*-based cloning techniques which are currently available. *Escherichia coli* plasmids, for example pBR322, contain the origin of replication from *Escherichia coli* and an *Escherichia coli* genetic marker which brings about resistance to an antibiotic or antibiotics, such as tetracycline and ampicillin. Such plasmids can be used advantageously in constructing the yeast hybrid vectors mentioned above.

Accordingly, the plasmid according to the invention contains in sequence: (1) a yeast-derived promoter, (2) an albumin-encoding region placed under control of said promoter, (3) a terminator for terminating transcription, which follows said region, and (4) a sequence homologous to a part of the yeast host chromosomal sequence. Preferably, the plasmid further contains (5) a signal sequence for secretory production present immediately downstream from the promoter, (6) a selective genetic marker for *Escherichia coli* transformant selection present immediately downstream from the homologous sequence and immediately downstream therefrom, (7) a selective genetic marker for yeasts. More preferably, the plasmid further contains (8) an *Escherichia coli* replication origin disposed immediately downstream from the selective genetic marker for *Escherichia coli* transformant selection. This plasmid is substantially free of the origin of replication in yeasts.

The above-described constituent sequences used for the plasmid of the present invention is avaivable from known plasmids. The plasmid of the present invention can be constructed in a conventional manner, for example, by excising the desired constituent sequence from the respective plasmid by cleavage with an appropriate restriction enzyme, ligating each constituent sequence in the determined order and introducing the ligation product into an appropriate vector plasmid. Alternately, the plasmid can be constructed by introducing the constituent sequences into the plasmid containing the other constituent sequence. Usable as the vector plasmid is an *Escherichia coli* plasmid such as pUC19, pBR322 or pAT153.

In the practice of the invention, a yeast, particularly a strain of the genus Saccharomyces or Pichia, is used as the host. The host should preferably be an auxotrophic and/or antibiotic-susceptible strain.

An albumin-producing transformant can be produced using the above-mentioned recombinant plasmid in the following manner.

The recombinant plasmid is integrated into the chromosome of the host yeast cell. The integration of the plasmid into the yeast chromosome can be performed in accordance with the method as described in Methods in Enzymology, 101, 228 (1983). Particularly, it is desirable that the plasmid be cleaved at an optionally selected site within that sequence contained therein and homologous to a part of the host yeast cell chromosome by treatment with an appropriate restriction enzyme and the thus-linearized plasmid be introduced into the host. The linearized plasmid is integrated into that region on the host yeast cell chromosome which is homologous to the region inserted In the plasmid. The linearized plasmid is integrated into the host chromosome with higher frequency as compared with the circular form. The yeast host to be used is preferably a mutant which has a mutation to which the selective marker gene for yeast selection contained in the plasmid is complementary, for example *Saccharomyces cerevisiae* AH22 (a, his4, leu2, can1) which is an leucine- and histidine-requiring, G418-susceptible strain.

The transformation of host yeast cells is carried out by an appropriate known method, for example by the protoplast-polyethylene glycol method or the electroporation method.

Whether the plasmid has been integrated at an expected site and whether the gene introduced is stable should then be checked. More particularly, that the plasmid has been integrated at the expected site can be confirmed by the Southern blotting technique using, as the probe, that sequence homologous to a part of the chromosomal sequence of the host yeast cell as was used for the purpose of transformation. As regards the stability of the albumin-encoding gene, the yield of albumin and the recovery from auxotrophy and maintenance of prototrophy are used as indices and it should be confirmed that these indices will not change even after scores of generations of subcultivation of the transformant in a nonselective medium.

A strain which meets the requirements of the above identification or confirmation tests is without doubt a transformant in which the albumin-encoding region-containing plasmid has been integrated into the host yeast cell chromosome at the desired site thereon. This transformant can be again transformed with another albumin-encoding region-containing plasmid using said transformant as the host. In this case, the region homologous to a part of the yeast cell chromosomal sequence may be different from the homologous region used in the first transformation. The first plasmid and the second plasmid may be same or different.

As different useful sequences homologous to a part of the host yeast cell chromosomal sequence, there may be mentioned the ribosome DNA and Ty element (transposon of yeast element). Since each yeast cell contains these genes each in plurality, the use of such genes makes it possible to integrate the desired gene into the host chromosome at a plurality of sites thereon by one transformation procedure.

By way of example, a typical method of integration is described below. It is to be noted, however, that the technique described is merely one of preferred means and is by no means limitative of the scope of the present invention. Homologous sequence substitution is possible by selective repetition.

*Saccharomyces serevisiae* AH22, which is a leucine- and histidine-requiring, G418-susceptible strain having mutations in LEU2 of the leucine synthesis gene and HIS4 of the histidine synthesis gene, is used as the host.

First, the strain is transformed with a plasmid containing LEU2 as the sequence homologous to a part of the host yeast cell chromosomal sequence to give a non-leucine-requiring transformant. The transformant obtained carries the albumin-encoding region-containing plasmid inserted at the LEU2 gene site on the chromosome, requires leucine no longer and can grow in leucine-free medium.

This transformant is then used as the host and transformed with a plasmid having HIS4, the gene for rendering the resulting transformant non-histidine-requiring, as the sequence homologous to a part of the host yeast cell chromosomal sequence (the plasmid of course containing an albumin-encoding region). The thus-obtained transformant carries the albumin-encoding region-containing plasmid inserted at the HIS4 gene site on the chromosome and is now a non-histidine-requiring strain capable of growing in histidine-free medium. At this time point, the desired gene to be expressed, namely the albumin gene, has been integrated at two sites, namely LEU2 and HIS4.

Then, the above transformant which requires neither leucine nor histidine any longer is used as the host and transformed with a plasmid having TRP1 as the sequence homologous to a part of the host yeast cell chromosomal sequence. This plasmid additionally contains the G418 resistance gene, as well as the albumin-encoding region. The transformant thus obtained carries the albumin-encoding region- and G418 resistance gene-containing plasmid inserted at the TRP1 gene site on the chromosome, so that it exhibits resistance to the antibiotic G418. This transformant thus contains the albumin gene at a total of three sites, namely LEU2, HIS4 and TRP1, on the chromosome. In producing said transformant, the order of integration is not particularly critical.

If a strain requiring a number of nutrients or a strain susceptible to a number of antibiotics is available, the corresponding number of regions can serve as sites for integration of a useful gene.

In this way, a desired gene can be inserted into the host chromosome at a plurality of sites. Each gene integrated into the chromosome can be maintained stably without being lost and the gene integration at a plurality of sites makes it possible to procuce the desired product in large amounts.

The transformant is cultivated in a known medium, for example YPD liquid medium [1% yeast extract (Difco), 2% Bacto-polypeptone (Difco), 2% glucose]. Generally, the cultivation is carried out at a temperature of 15°–43° C. (preferably about 30° C.) for about 20 to 100 hours, with aeration and/or stirring as necessary.

After cultivation, the product albumin is purified by a per se known method, for example by fractionation, chromatography, etc.

The assay for albumin can be performed by using an RPHA or ELISA technique.

The following example illustrates the invention in further detail but is by no means limitative of the scope of the present invention.

The reaction, analysis and other techniques used are well known in the art. Unless otherwise indicated, the enzymes used are available from commercial sources, for example, New England BioLabs (NEB), Massachusetts, USA; Amersham, Great Britain; and Bethesda Research Laboratories (BRL), Maryland, USA.

Unless otherwise specified, the enzymatic reactions were carried out using those buffers and reaction conditions that are recommended by the manufacturers of the respective enzymes.

The transformation of *Escherichia coli* with each plasmid, plaque hybridization, electrophoresis and DNA recovery from gels were performed by the methods described in "Molecular Cloning", Cold Spring Harbor Laboratory (1982). The transformation of yeast was carried out by the method described in "Methods in Yeast Genetics", Cold Spring Harbor Laboratory (1981).

EXAMPLE 1

[I] Cloning of GAPDH promoter region, SUC2 signal region, LEU2region, HIS4region, TRP1 region and PH05 terminator region and preparation of HSA gene and G418 resistance gene The above regions and genes were prepared by the methods described in the literature or modifications thereof or purchased from commercial sources, as follows:

GAPDH promoter: Holland, H. J. and Holland, J. P., J. Biol. Chem., 254 (12), 5466 (1979); Holland, H. J. and Holland, J. P., J. Biol. Chem., 254 (19), 9839 (1979); U.S. patent application Serial No. 057,143 now U.S. Pat. No. or EP-A-248410;

SUC2 signal sequence: U.S. patent application Ser. Nos. 488,337 now abandoned and 057,143 now U.S. Pat. No. 4,945,046 corresponding to EP-A-127304 and EP-A-248410, respectively;

HSA gene: U.S. patent application Ser. No. 745,524 now abandoned or EP-A-206733;

PH05 terminator: U.S. patent application Ser. No. 296, 868 now abandoned or EP-A-216573;

G418 resistance gene: Oka, A., Sugisaki, H. and Takanami,

M., J. Mol. Biol., 147, 217 (1981);

Jimenez, A. and Davies, J., Nature, 287, 869 (1980); U.S. patent application Ser. No. 612,796 or EP-A-163491;

TRP1: Derived from the plasmid pBTI-10 (commercially available from Boehringer-Mannheim);

LEU2: Derived from the plasmid pBTI-1 (commercially available from Boehringer-Mannheim);

HIS4: Donahue, T. F., Daves, R. S. et al., Cell, 32, 89 (1983).

*Escherichia coli* replication origin region and ampicillin resistance gene: derived from the plasmid pUC19 (commercially available from Takara Shuzo).

[II] Plasmid construction

The construction of the plasmids were carried out using the conventional methods described in "Molecular Cloning", Cold Spring Harbor Laboratory (1982).

1. Construction of plasmid pYI011

A yeast genomic DNA was prepared from *Saccharomyces cerevisiae* GRF18 pho80 cir° (EP-A-180958).

This genomic DNA was digested with HincII and BamHI and the 2.3–3.2 kb DNA fragments were isolated by agarose gel electrophoresis. These DNA fragments were inserted into the HincII and BamHI site of plasmid pUC18. The resulting plasmids were introduced into *Escherichia coli* JM109 competent cells. Thus, about 7,500 colonies for the yeast genomic DNA library were obtained.

Separately, the DNA sequence shown below, which coded for a part of a yeast invertase structural gene, was synthesized.

Thr Ser Asp Arg Pro Leu Val His Phe Thr Pro Asn Lys Gly

5'-ACT AGC GAT AGA CCT TTG GTC CAC TTC ACA CCC
AAC AAG GGC Trp Met Asn TGG ATG AA-3'

The yeast genomic DNA library was screened using the above synthetic DNA as a probe. Among the positive clones (the detection ratio=1/360), a clone having a plasmid which contains the promoter and signal sequence region of a yeast invertase (SUC2) gene was selected. This plasmid was named pYI011.

2. Construction of plasmids pYI013, pYI014 and pYI016 (cf. FIGS. 1A–1D)

The DNA sequence encoding the SUC2 signal sequence was synthesized. Its DNA base sequence is shown below.

```
                                    Met  Leu  Leu  Gln  Ala  Phe
5'-AGCTTTTCTTTTCACTAACGTATATG       ATG  CTT  TTG  CAA  GCT  TTC
  3'-AAAGAAAAGTGATTGCATATAC         TAC  GAA  AAC  GTT  CGA  AAG
    HindIII                                                     HindIII
Leu  Phe  Leu  Leu  Ala  Gly  Phe  Ala  Ala  Lys  Ile  Ser  Ala
CTT  TTC  CTT  TTG  GCT  GGT  TTT  GCA  GCC  AAA  ATA  TCT  GCA
GAA  AAG  GAA  AAC  CGA  CCA  AAA  CGT  CGG  TTT  TAT  AGA  CGT
GATCTGCT-3'
CTAGACGAGATC-5'
BglII    XbaI
```

This synthetic DNA was ligated with the pYI011-derived 880 bp EcoRI-HindIII DNA fragment and the ligation product was inserted into the EcoRI-XbaI site of pUC19. The resulting plasmid (pYI012) was subjected to digestion with BglII, treatment with mung bean nuclease and further digestion with EcoRI. The 0.97 kb DNA fragment was isolated.

Separately, the following DNA fragments, A-1 and A-2, were synthesized.

A-1 (35 mer)

5'-TCGACGCACACAAGAGTGAGGTTGCTCATCGGTTT-3'

A-2 (31 mer)

5'-AAACCGATGAGCAACCTCACTCTTGTGTGCG-3'

These DNA fragments were annealed to each other and the annealing product was ligated to the DNA fragment obtained by digesting pGX-1043 (Genex) with DraI and XbaI to obtain plasmid pKO-001. This plasmid was digested with HincII and XbaI to obtain the 1 kb HincII-XbaI DNA fragment. This DNA fragment was ligated with the above-obtained 0.97 kb DNA fragment.

Separately, pGX-1043 was digested with XbaI and HindIII and the digestion product was inserted into pUC19 at the XbaI-HindIII site. This plasmid (pKM-001) was digested with HindIII and the cohesive ends of the resulting DNA fragment were filled in with T4 polymerase. Then, this was ligated with SalI linker to obtain plasmid pKO-002. This plasmid was subjected to digestion with EcoRI and XbaI. The 3.5 kb DNA fragment was isolated and ligated with the above-obtained ligation product. The thus-obtained plasmid was named plasmid pYI013.

Plasmid pYI013 was digested with EcoRI and SalI, and the 2.75 kb DNA fragment was isolated. The cohesive ends of the DNA fragment was rendered blunt using DNA polymerase I Klenow fragment. The DNA fragment was ligated with the BamHI linker and the ligation product was digested with BamHI. The resulting DNA fragment was ligated with the BamHI digest (8.7 kb) of plasmid pHIN/G-2 (Biogen) and the resulting plasmid was named pYI014.

Separately, the above-described BamHI digest (8.7 kb) was self-ligated to give plasmid pYI016.

Figure 2A:
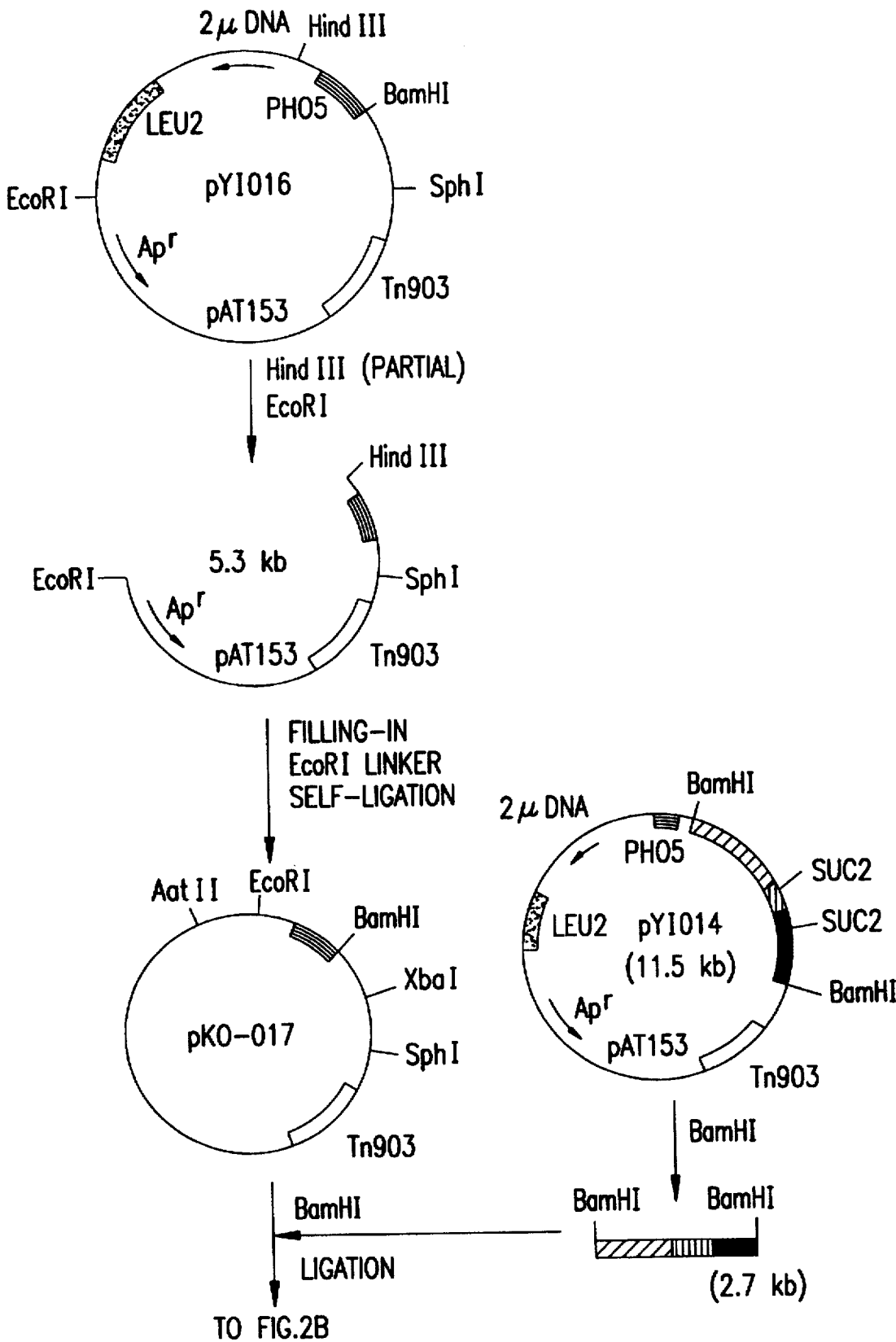
FIGS. 2A–2B show a process for constructing the plasmids pYO-020 and pYO-026.
Figure 2B:
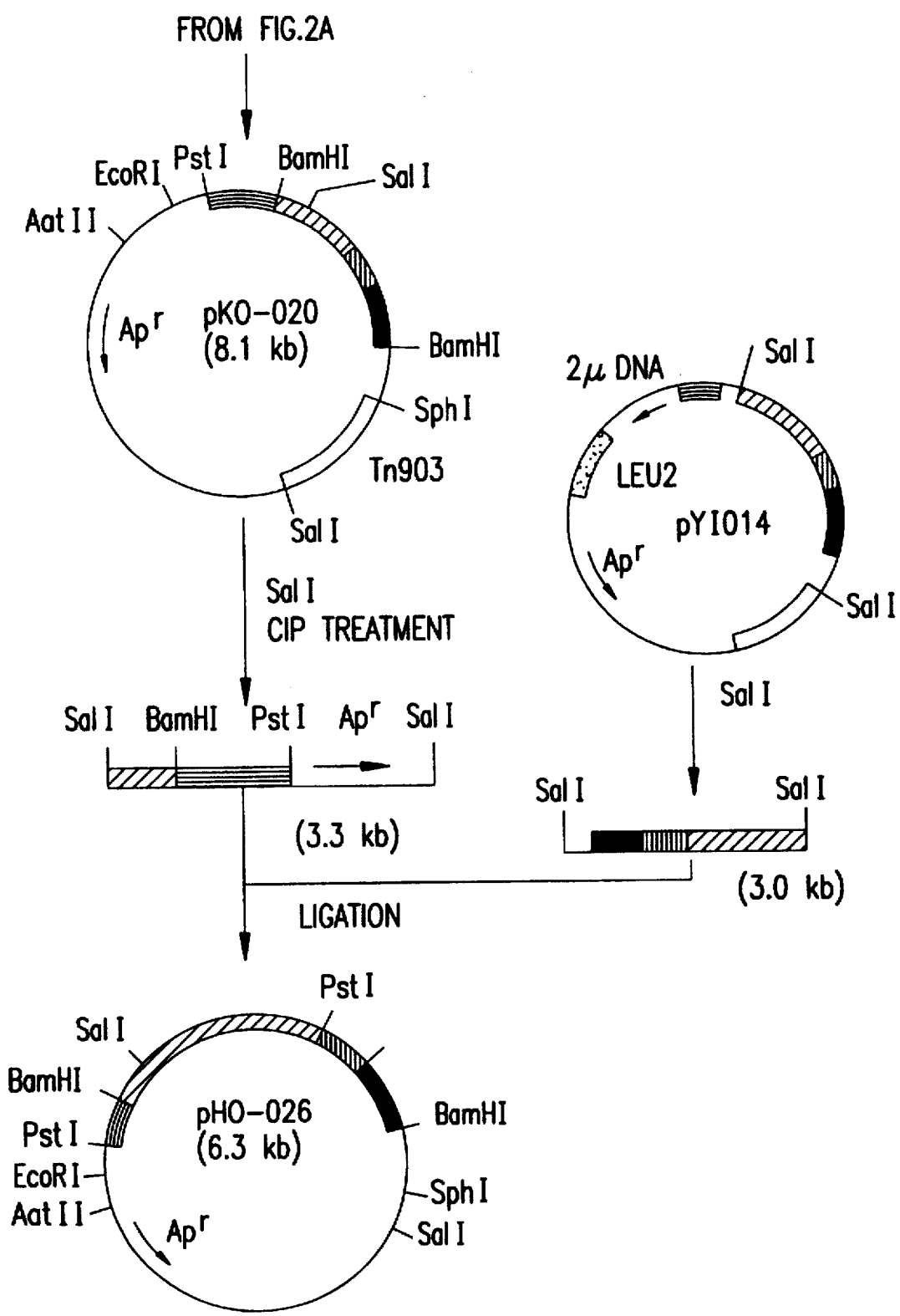

3. Construction of plasmids pKO-020 and pKO-026 (cf. FIGS. 2A–2B)

Plasmid pYI016 was partially digested with HindIII and subsequently digested with EcoRI. The 5.3 kb DNA fragment was isolated and the cohesive ends were filled in with Klenow fragment of DNA polymerase I. This DNA fragment was ligated with the EcoRI linker and the ligation product was self-ligated to obtain plasmid pKO-017. This plasmid was digested with BamHI and the thus-obtained DNA fragment was ligated with the pYI014-derived 2.7 kb BamHI DNA fragment to obtain plasmid pKO-020.

Plasmid pYI014 was digested with SalI and the 3.0 kb DNA fragment was isolated. Separately, plasmid pKO-020 was digested with SalI to obtain the 3.3 kb DNA fragment and this DNA fragment was treated with calf intestine-derived alkaline phosphatase (CIP) for 5'-dephosphorylation. Then, the resulting DNA fragment was ligated with the above-obtained 3.0 kb DNA fragment to obtain plasmid pKO-026.

Figure 3A:
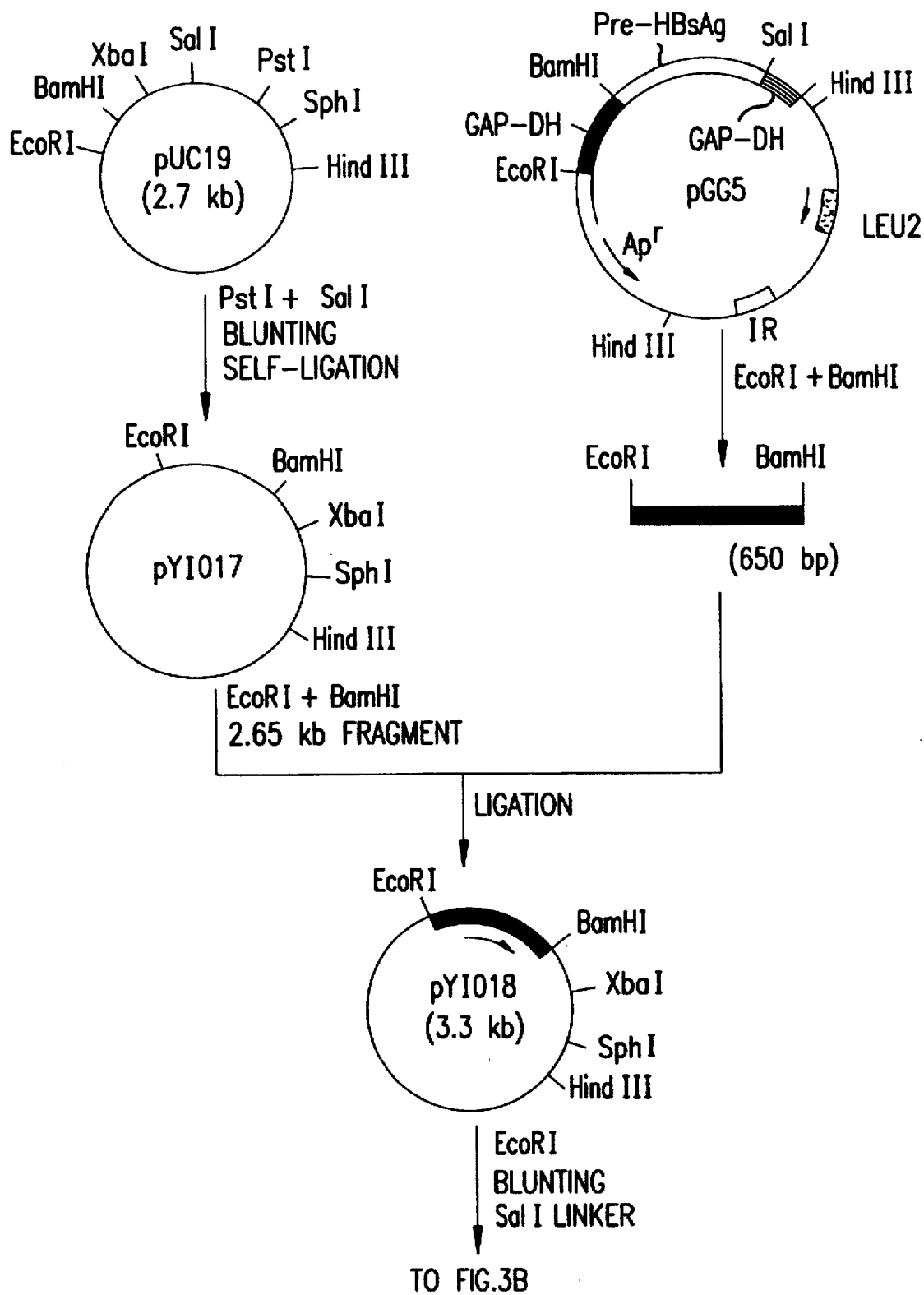
FIG. 3A–3C show a process for constructing the plasmid pKM-007.
Figure 3B:
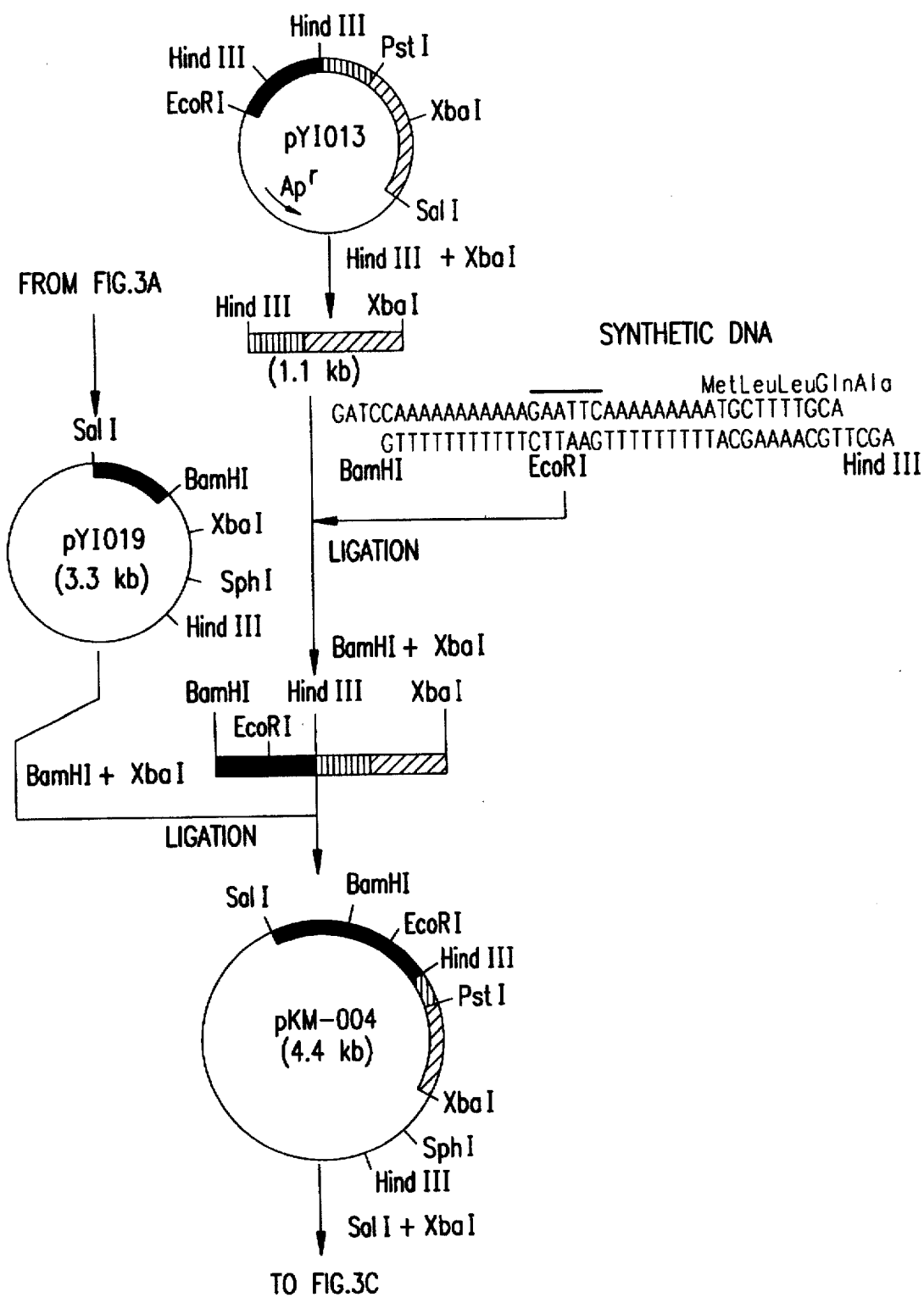
Figure 3C:
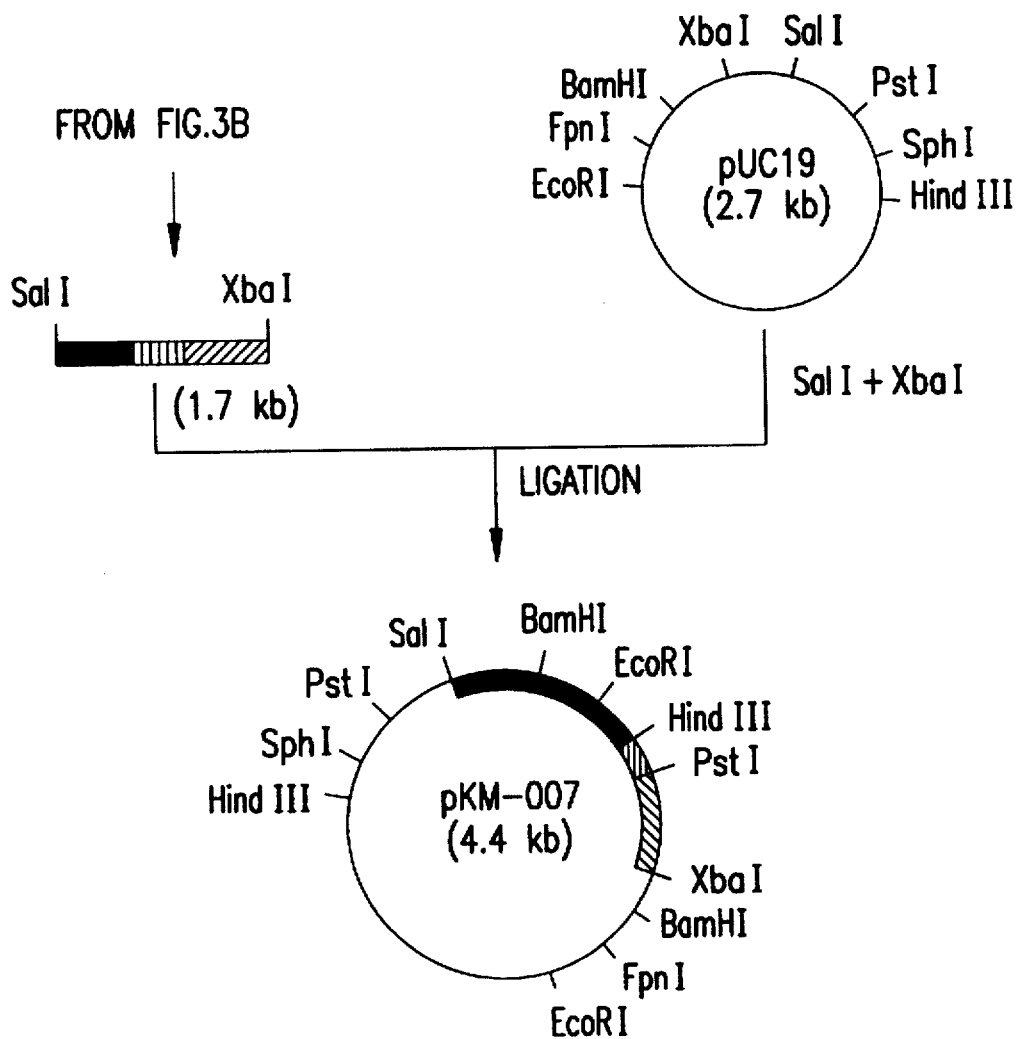

4. Construction of pKM-007 (cf. FIG. 3A–3C)

The commercially available plasmid pUC19 was digested with PstI and SalI. The cohesive ends of the resulting DNA fragment were made blunt using T4 DNA polymerase. After ligation, the circular plasmid was digested with EcoRI and BamHI and the 2.65 kb DNA fragment was isolated. Separately, plasmid pGG5 (JP-A-63-84498) was digested with EcoRI and BamHI and the 0.65 kb DNA fragment was isolated. This DNA fragment was ligated with the above-obtained 2.65 kb DNA fragment to obtain plasmid pYI018. This plasmid was digested with EcoRI and the cohesive ends of the thus-obtained DNA fragment was made blunt using T4 DNA polymerase, followed by ligation with SalI linker. This ligation product (pYI019) was digested with BamHI and XbaI.

Separately, the DNA sequence shown below, which coded for the GAP-DH promoter and a part of the SUC2 signal sequence was synthesized.

```
                                         MetLeuLeuGlnAla
GATCCAAAAAAAAAAAAGAATTCAAAAAAAAATGCTTTTGCA
     GTTTTTTTTTTTCTTAAGTTTTTTTTTACGAAAACGTTCGA
BamHI            EcoRI                    HindIII
```

The synthetic DNA was ligated with the pYI013-derived 1.1 kb HindIII-XbaI DNA fragment and the resulting DNA fragment was subjected to digestion with BamHI and XbaI and ligated with the above-obtained pYI019-derived to obtain plasmid pKM004. This was further digested with SalI and XbaI and inserted into the SalI-XbaI site of plasmid pUC19 to obtain plasmid pKM007 (4.4 kb).

Figure 4A:
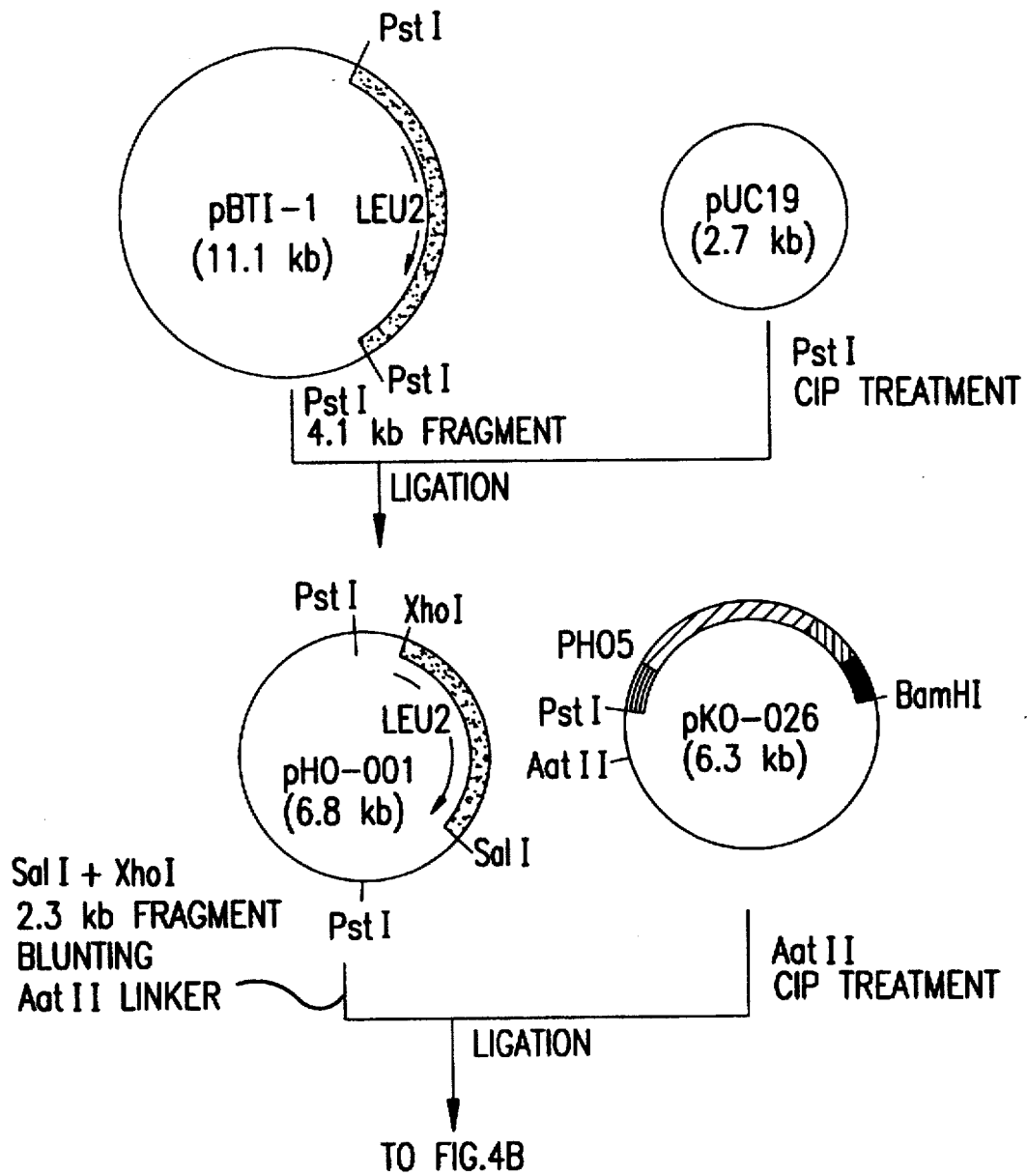
FIGS. 4A–B show a process for constructing the plasmid pMM-006.
Figure 4B:
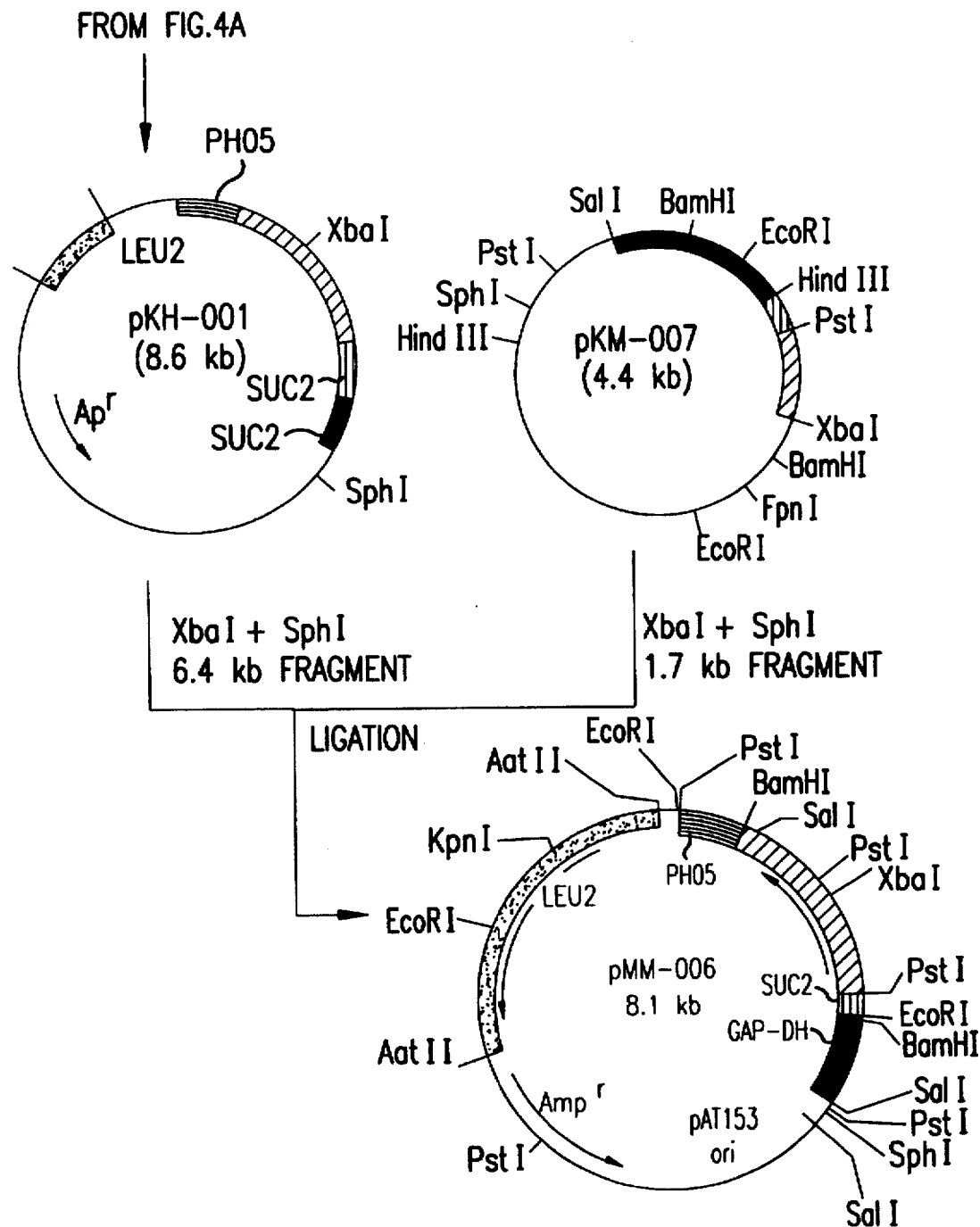
Figure 5A:
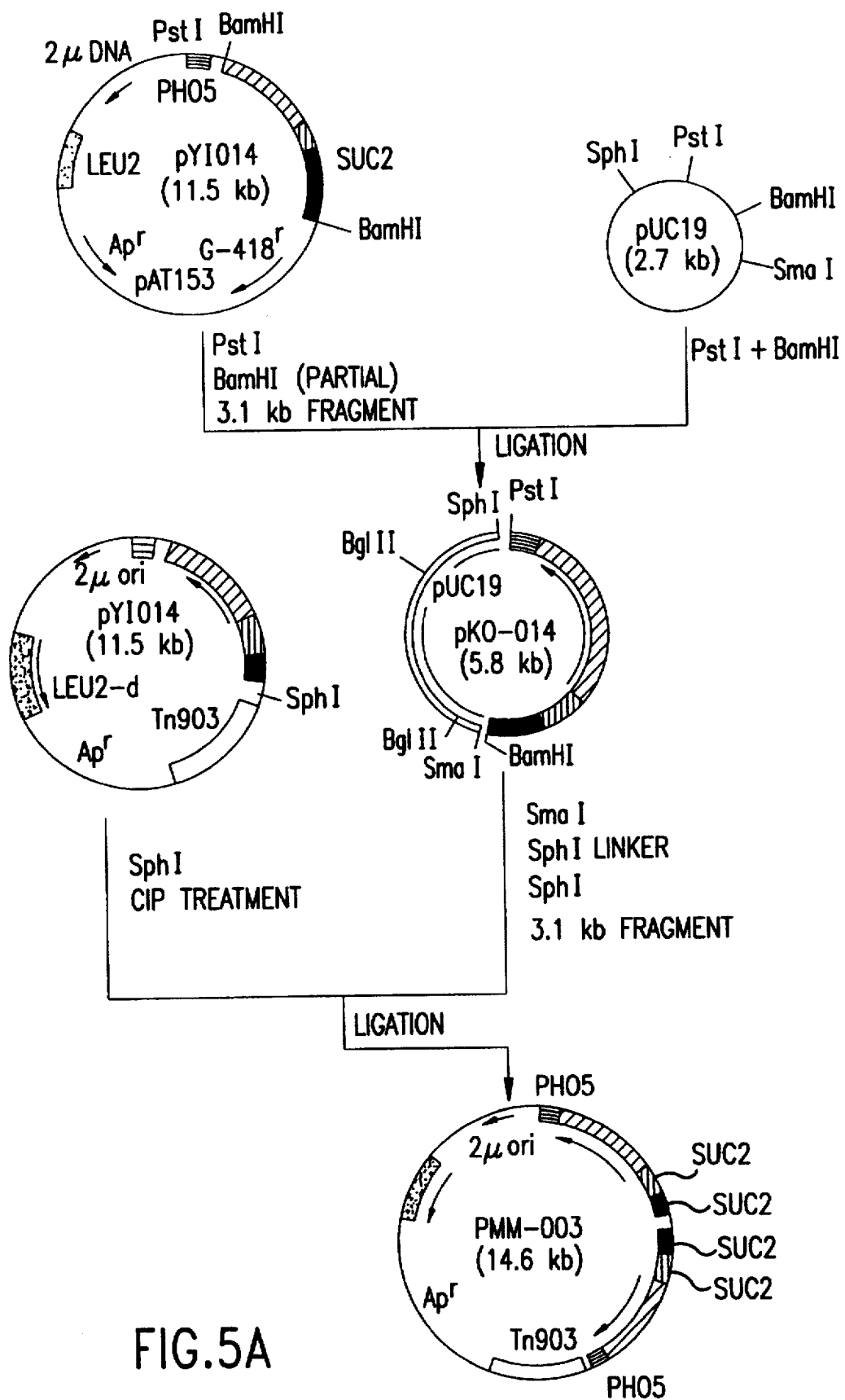
FIGS. 5A–5D show a process for constructing the plasmid pMS-008.
Figure 5B:
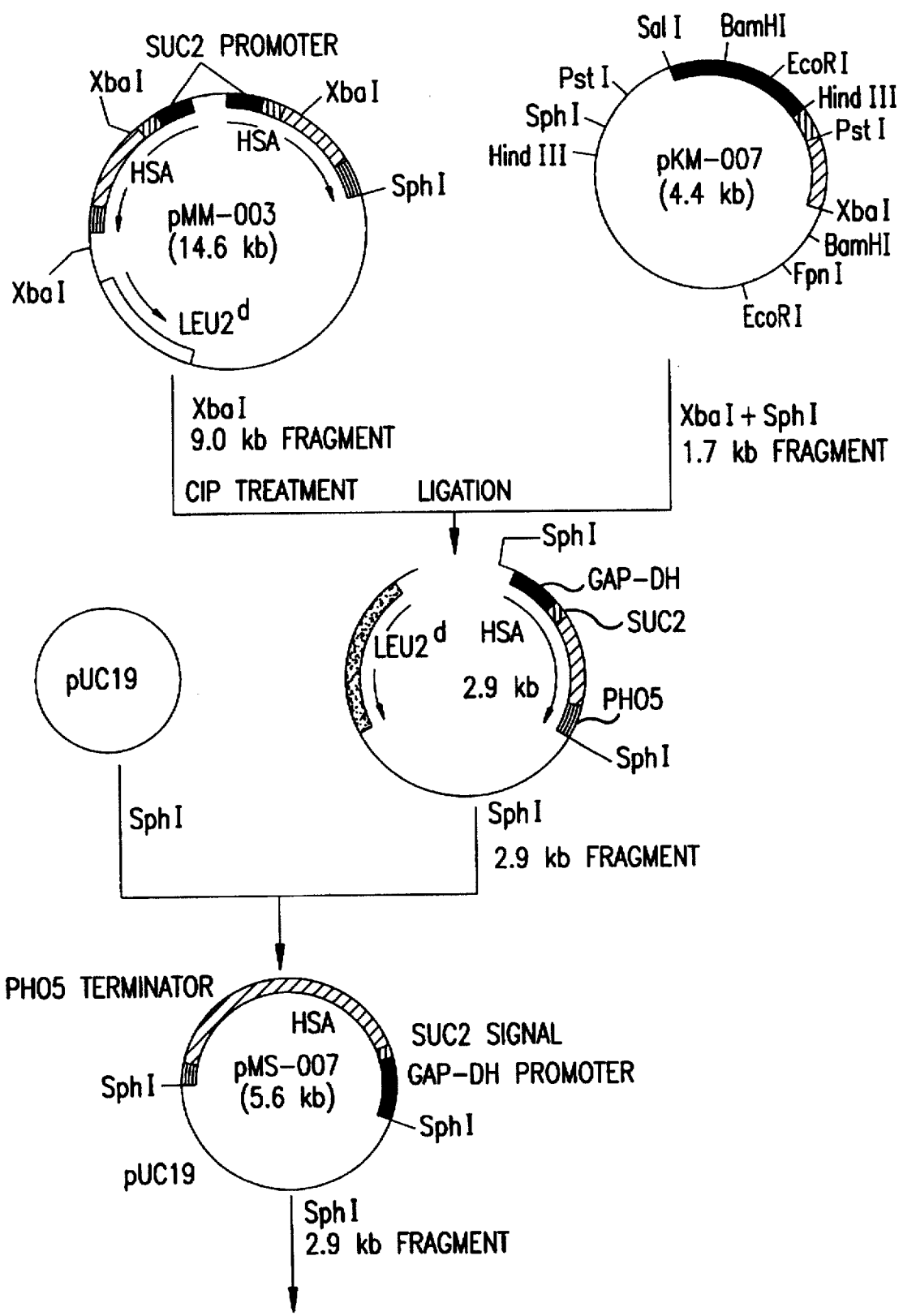
Figure 5C:
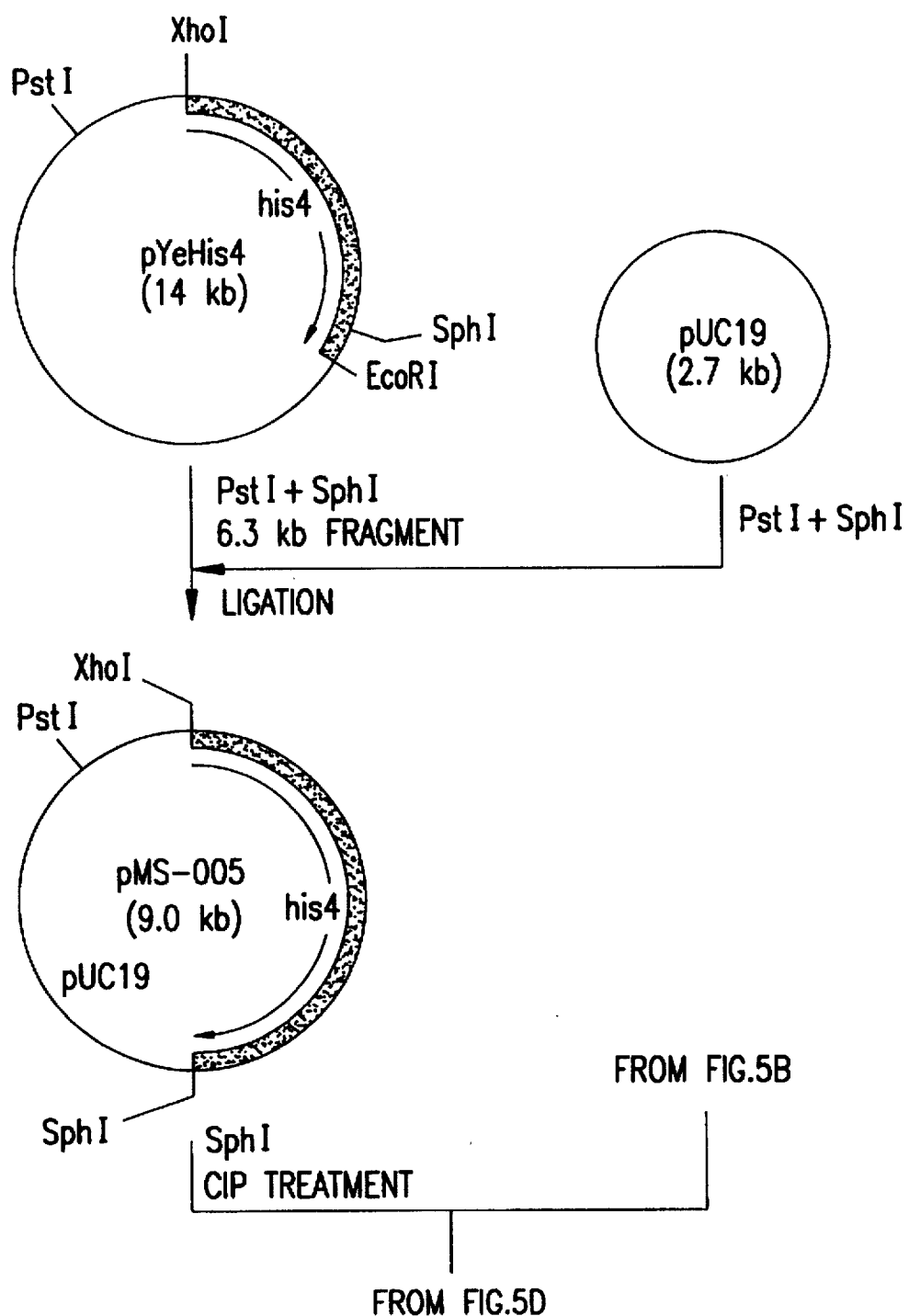
Figure 5D:
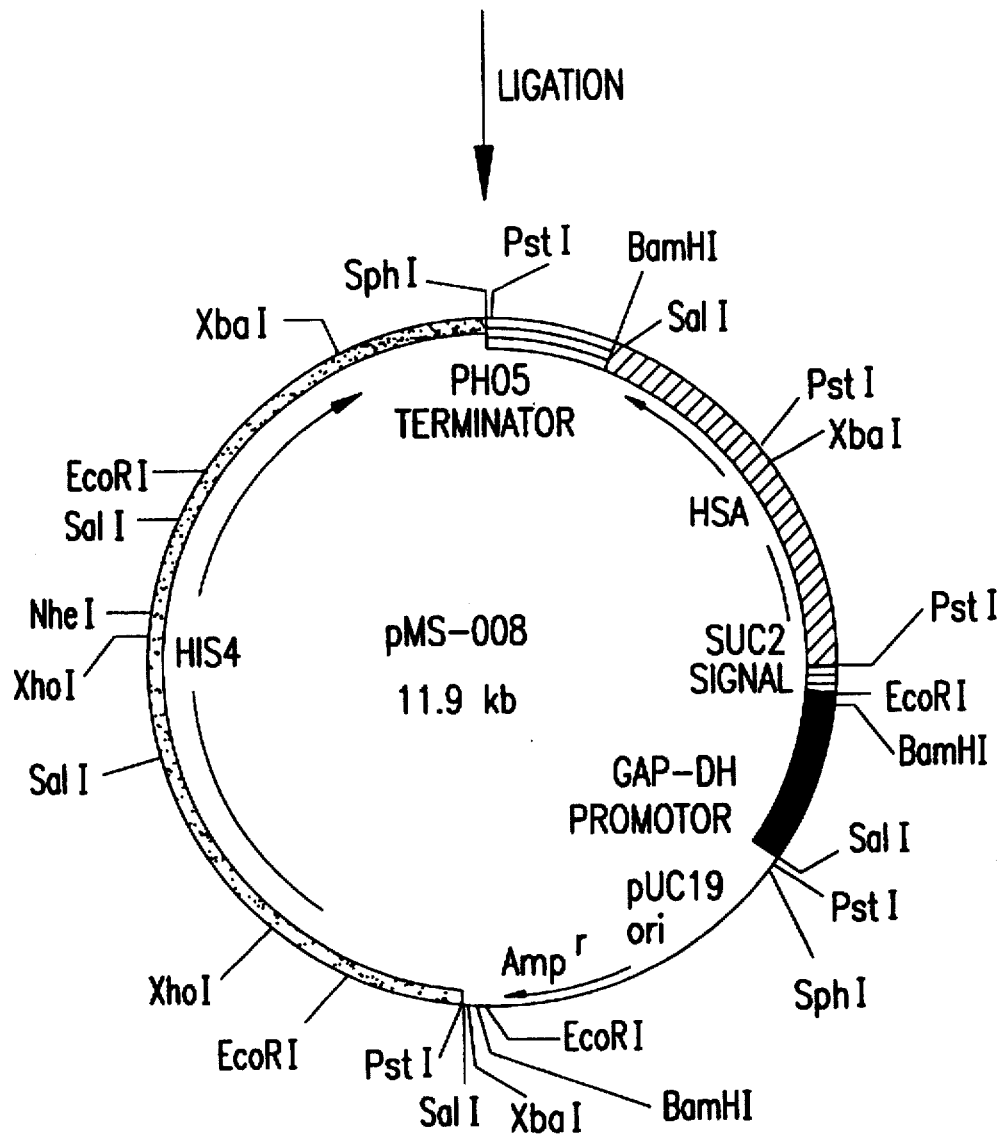

5. Construction of plasmid pMM-006 (cf. FIG. 4A–4B)

Plasmid pBTI-1 was digested with PstI to obtain 4.1 kb DNA fragment. Plasmid pUC19 was digested with PstI and the resulting DNA fragment was treated with CIP and ligated with the above-obtained 4.1 kb DNA fragment to obtain plasmid pHO-001 (6.8 kb).

Plasmid pHO-001 was digested with SalI and XhoI and the 2.3 kb DNA fragment was isolated. The cohesive ends of this DNA fragment were made blunt using Klenow fragment of DNA polymerase I, followed by ligation with the AatII linker.

Separately, plasmid pKO-026 was digested with AatII and the resulting 6.3 kb DNA fragment was treated with CIP and ligated with the above-obtained DNA fragment to obtain plasmid pKH001. This plasmid was digested with XbaI and SphI and the 6.4 kb DNA fragment was isolated.

Separately, plasmid pKM-007 was digested with XbaI and SphI to obtain the 1.7 kb DNA fragment. This fragment was ligated with the above 6.4 kb DNA fragment and plasmid pMM-006 was obtained.

The plasmid pMM-006 contains the coding region of the LEU2 gene as the sequence homologous to the sequence on the host yeast cell chromosome. In this plasmid, the SUC2 signal sequence, the structural gene for HSA and the PHO5 terminator are joined together under the control of the GAP-DH promoter.

6. Construction of plasmid pMS-008 (cf. FIG. 5A–5D)

Plasmid pYI014 was digested with PstI and BamHI and the thus-obtained 3.1 kb DNA fragment was inserted into the PstI-BamHI site of pUC19 to obtain plasmid pKO-014. This plasmid was digested with SmaI and the thus-obtained DNA fragment was ligated with the SphI linker and digestion with SphI was performed to give 3.1 kb DNA fragment.

Separately, pYI014 was digested with SphI and the resulting DNA fragment (11.5 kb) was treated with CIP for 5'-dephosphorylation. This was ligated with the above-obtained 3.1 kb DNA fragment to obtain plasmid pMM003.

The ligation product (pMM-003) was digested with XbaI and the 9.0 kb DNA fragment was isolated. After treatment with CIP, the 9.0 kb DNA fragment was ligated with the pKM-007-derived 1.7 kb XbaI-SphI DNA fragment. The ligation product was digested with SphI and the 2.9 kb DNA fragment was isolated.

Plasmid pYeHis4 (Proc. Natl. Acad. Sci. USA, 78(6), 3496 (1981) and Mol. Gen. Genet., 188, 44 (1982))) was digested with PstI and SphI and the 6.3 kb DNA fragment was isolated. This DNA fragment was inserted into the PstI-SphI site of pUC19 and digestion with SphI was performed. The thus-obtained DNA fragment was treated with CIP and ligated with the above 2.9 kb DNA fragment. Thus, plasmid pMS-008 was obtained.

The plasmid pMS-008 contains the coding region of the HIS4 gene as the sequence homologous to a part of the host yeast cell chromosomal sequence. In this plasmid, the SUC2 signal sequence, the structural gene for HSA and the PHO5 terminator are joined together under the control of the GAP-DH promoter.

Figure 6A:
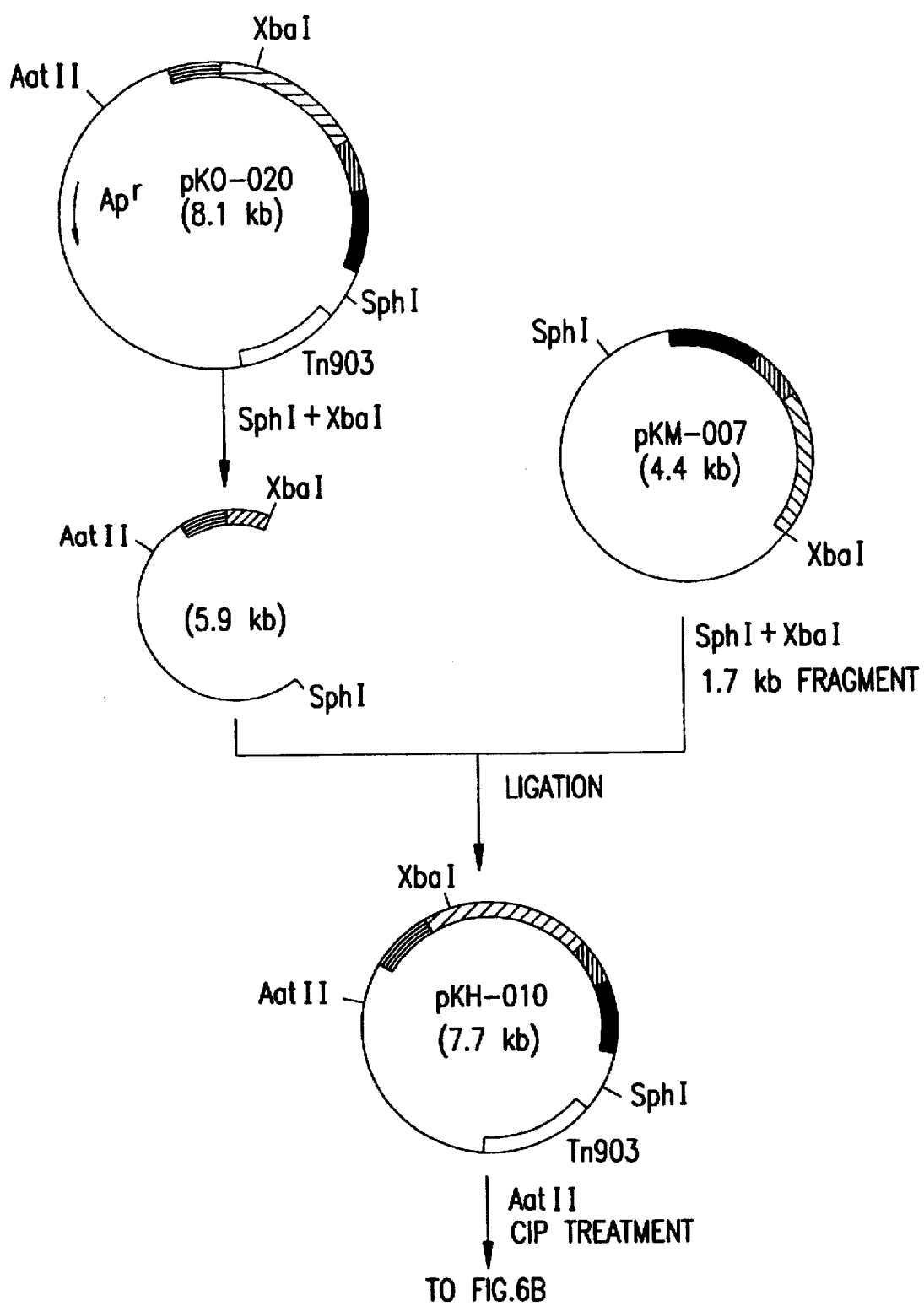
FIGS. 6A–6C show a process for constructing the plasmid pHO-011.
Figure 6B:
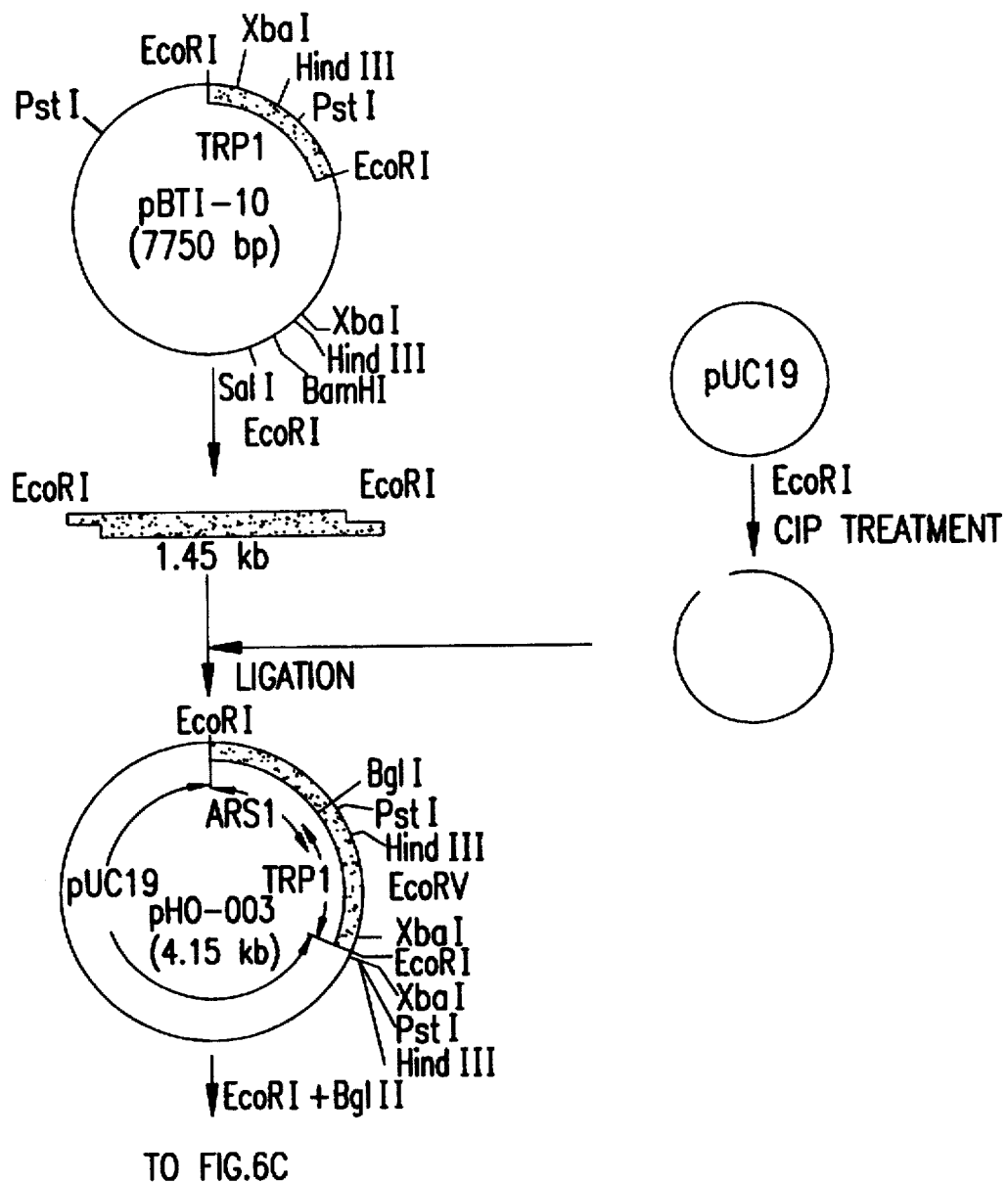
Figure 6C:
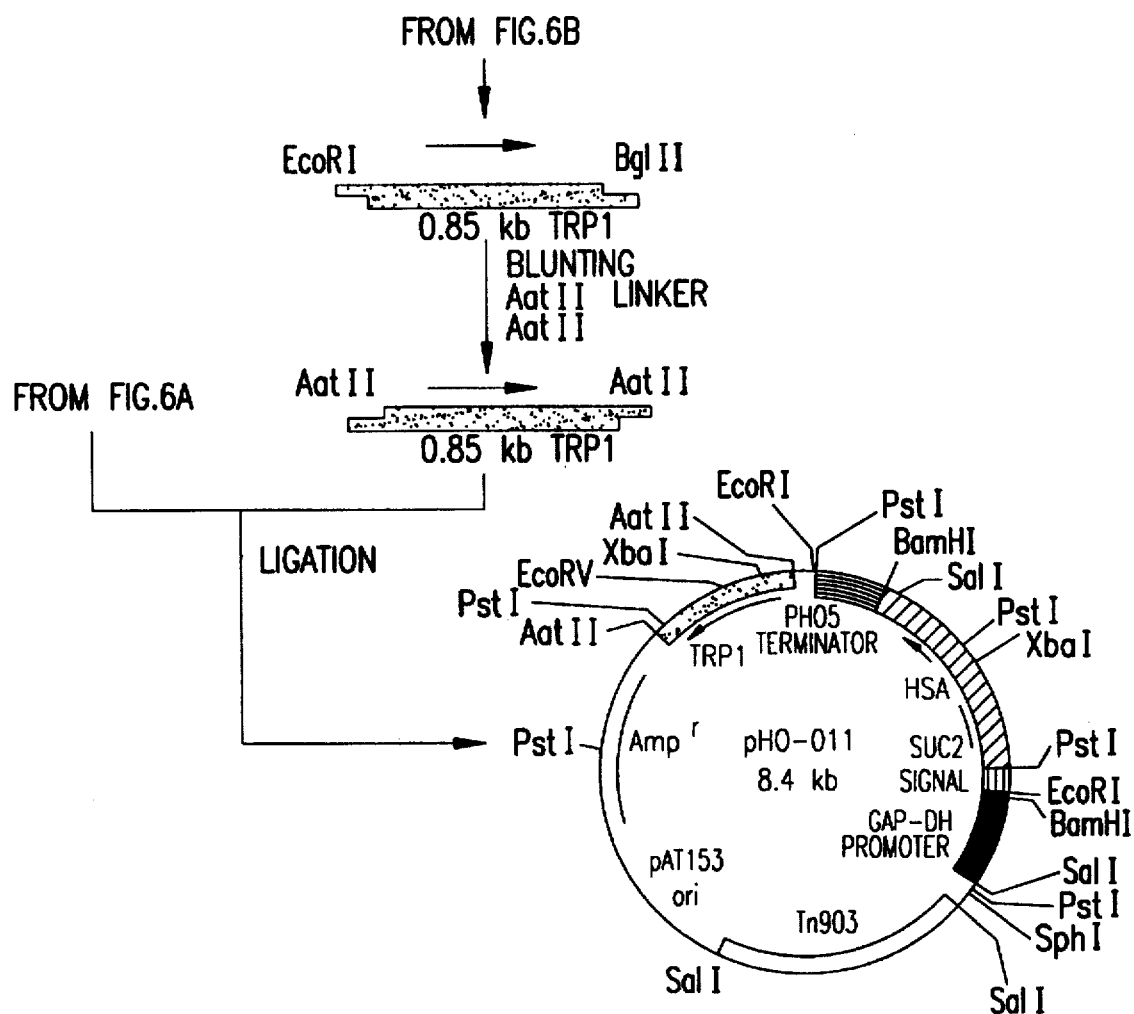
Figure 7A:
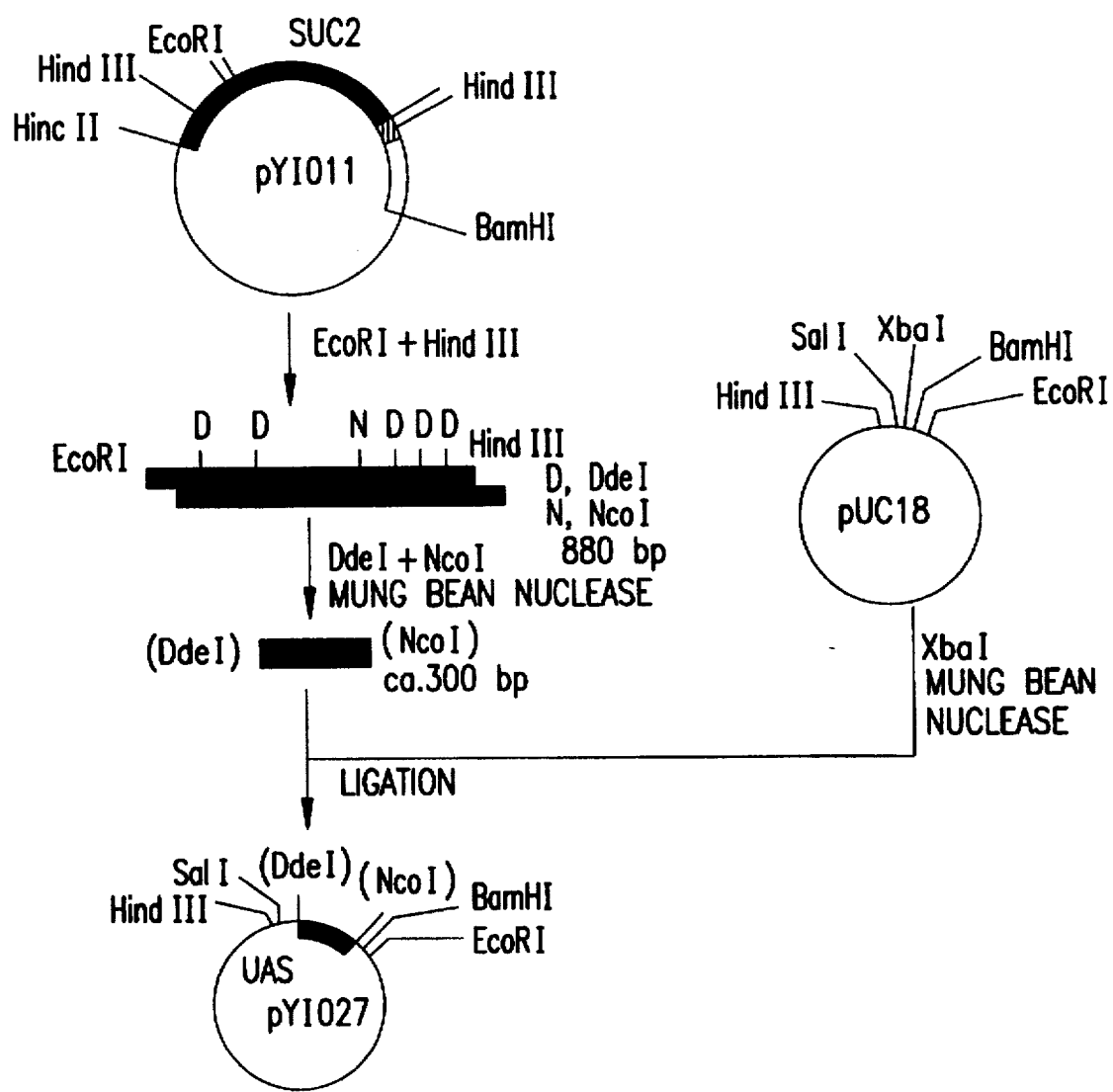
FIGS. 7A–7B show a process for constructing the plasmid pYI032.
Figure 7B:
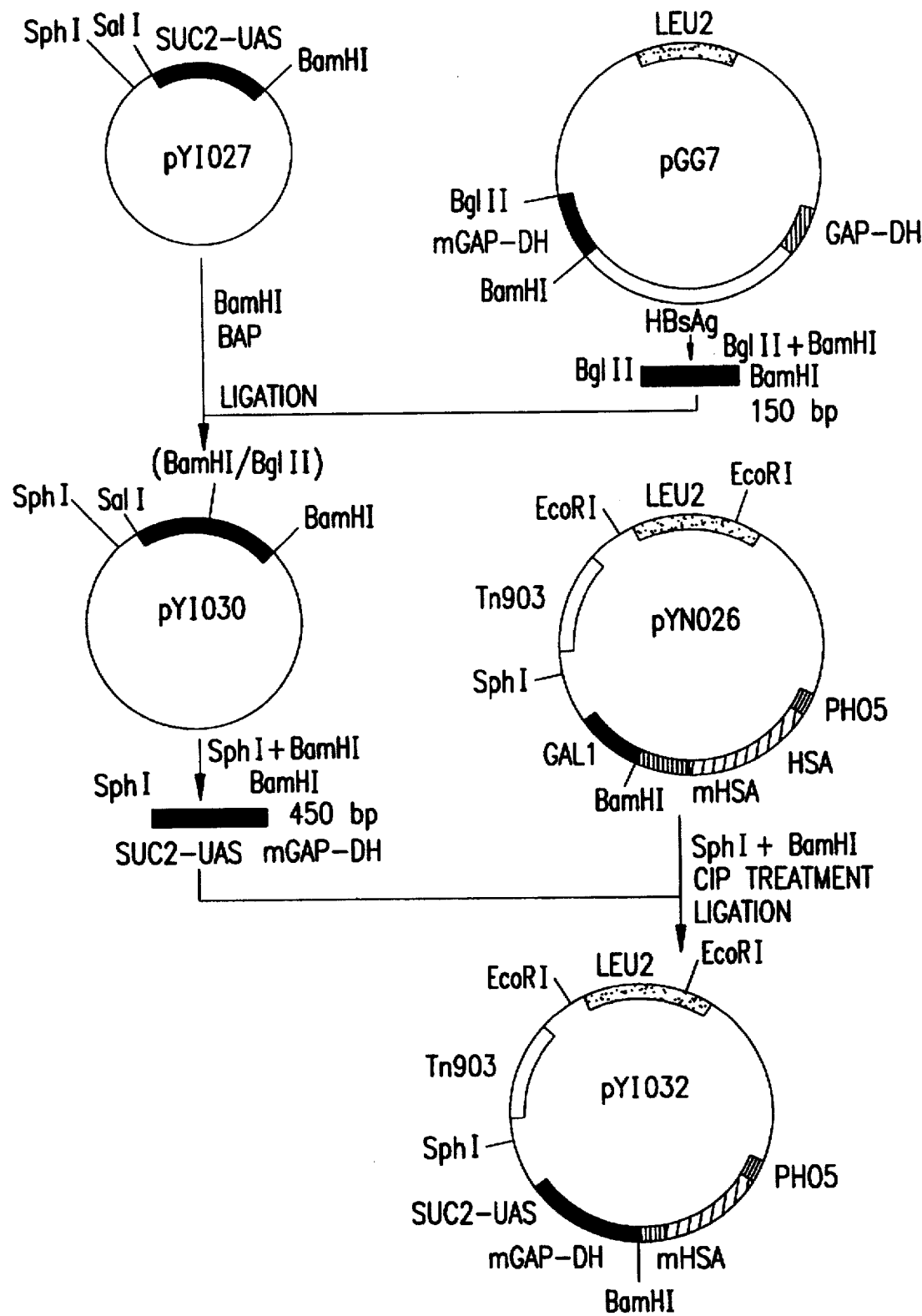
Figure 8A:
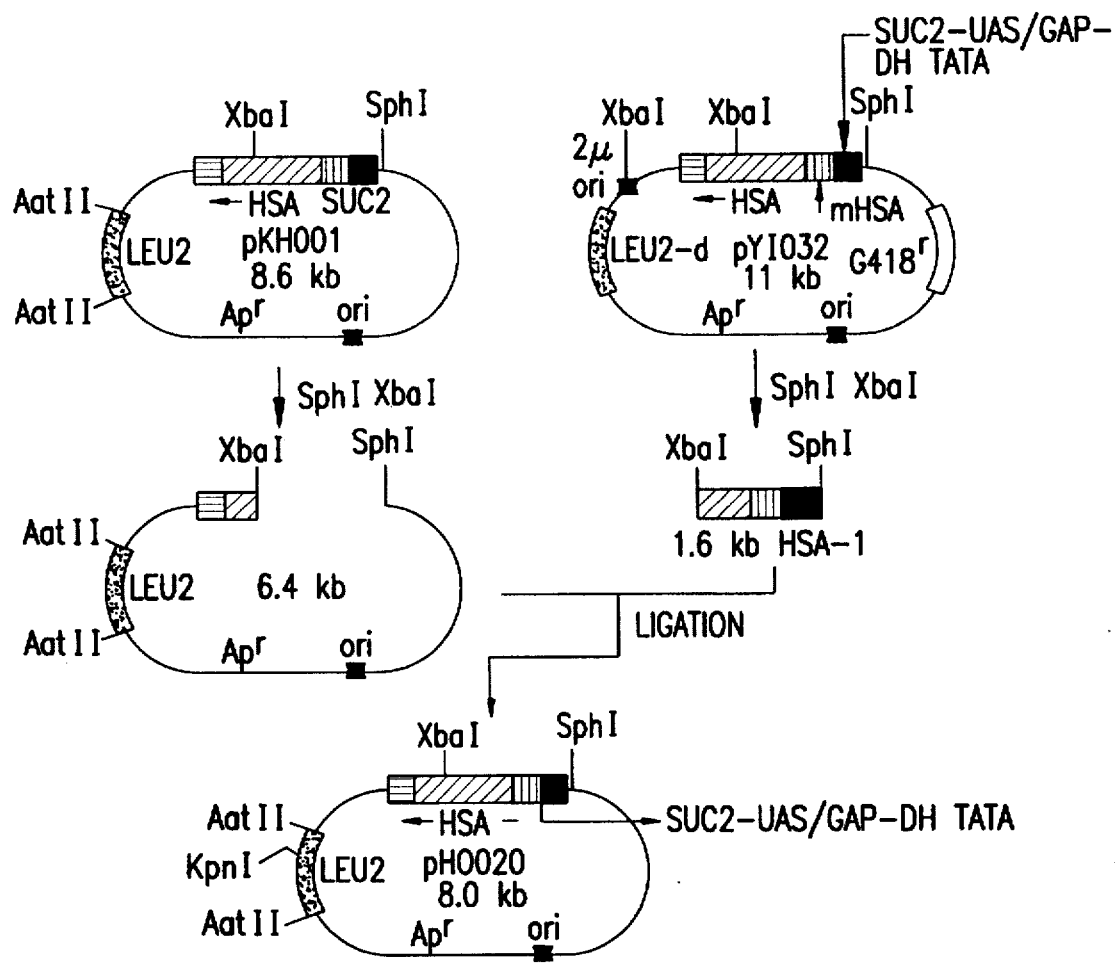
FIGS. 8A–8I show a process for constructing the plasmid pHRA33.
Figure 8B:
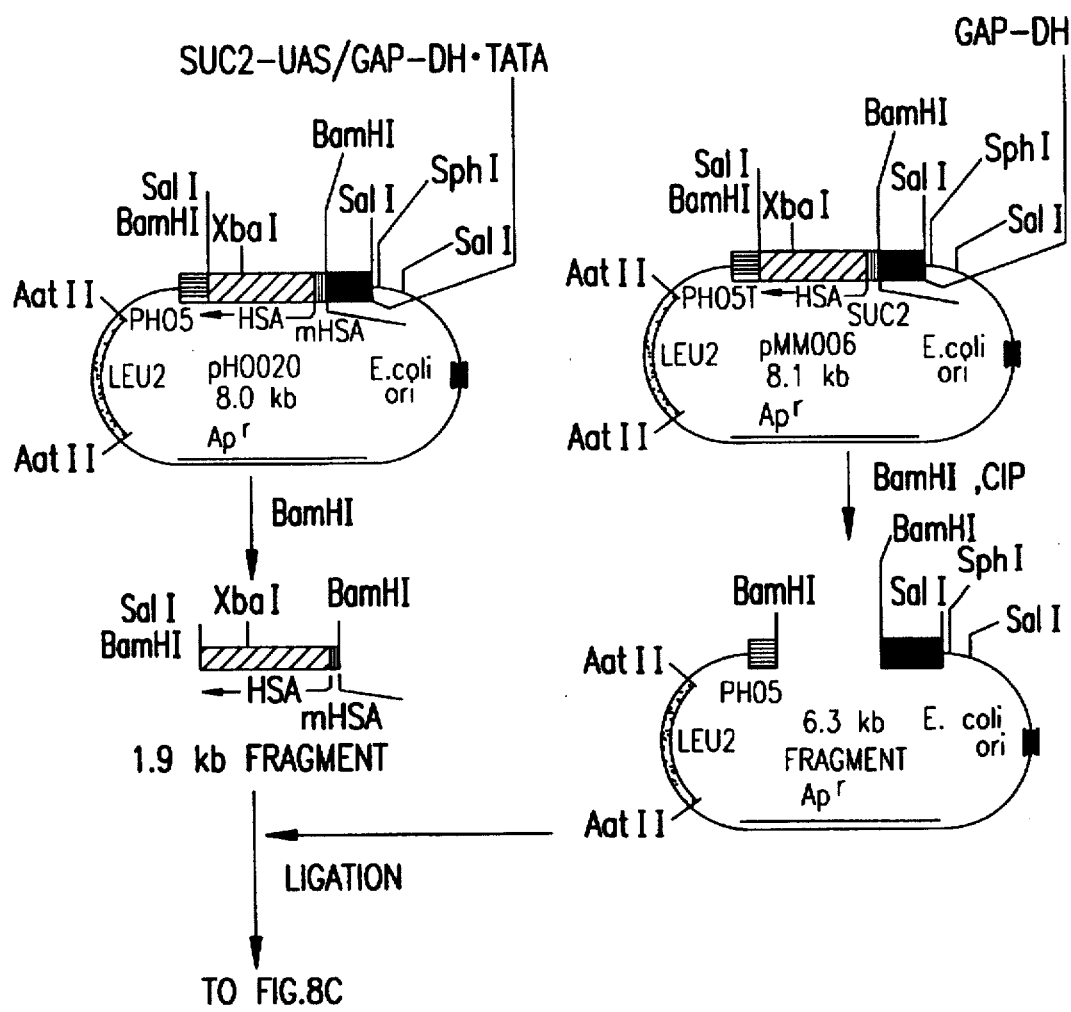
Figure 8C:
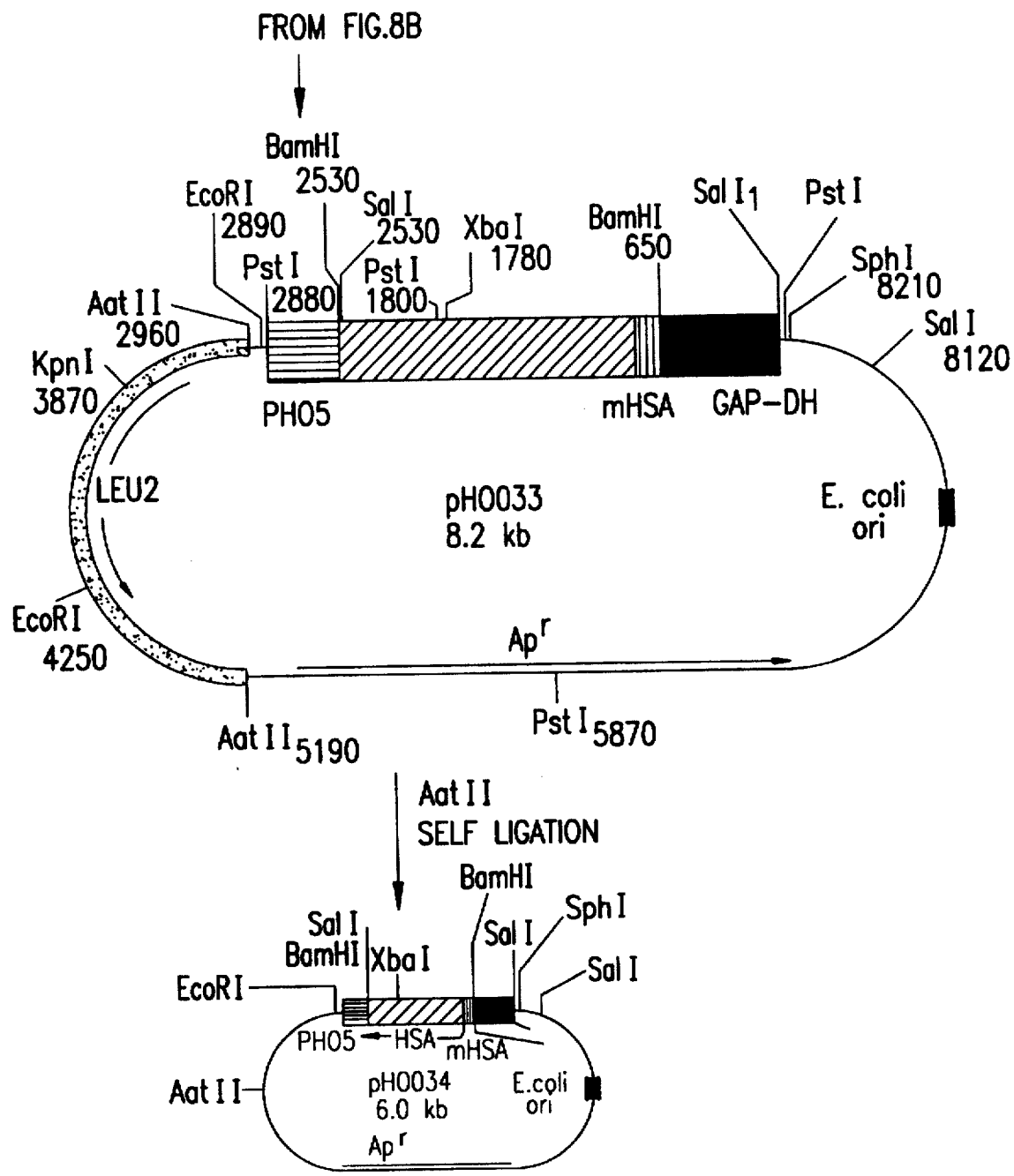
Figure 8D:
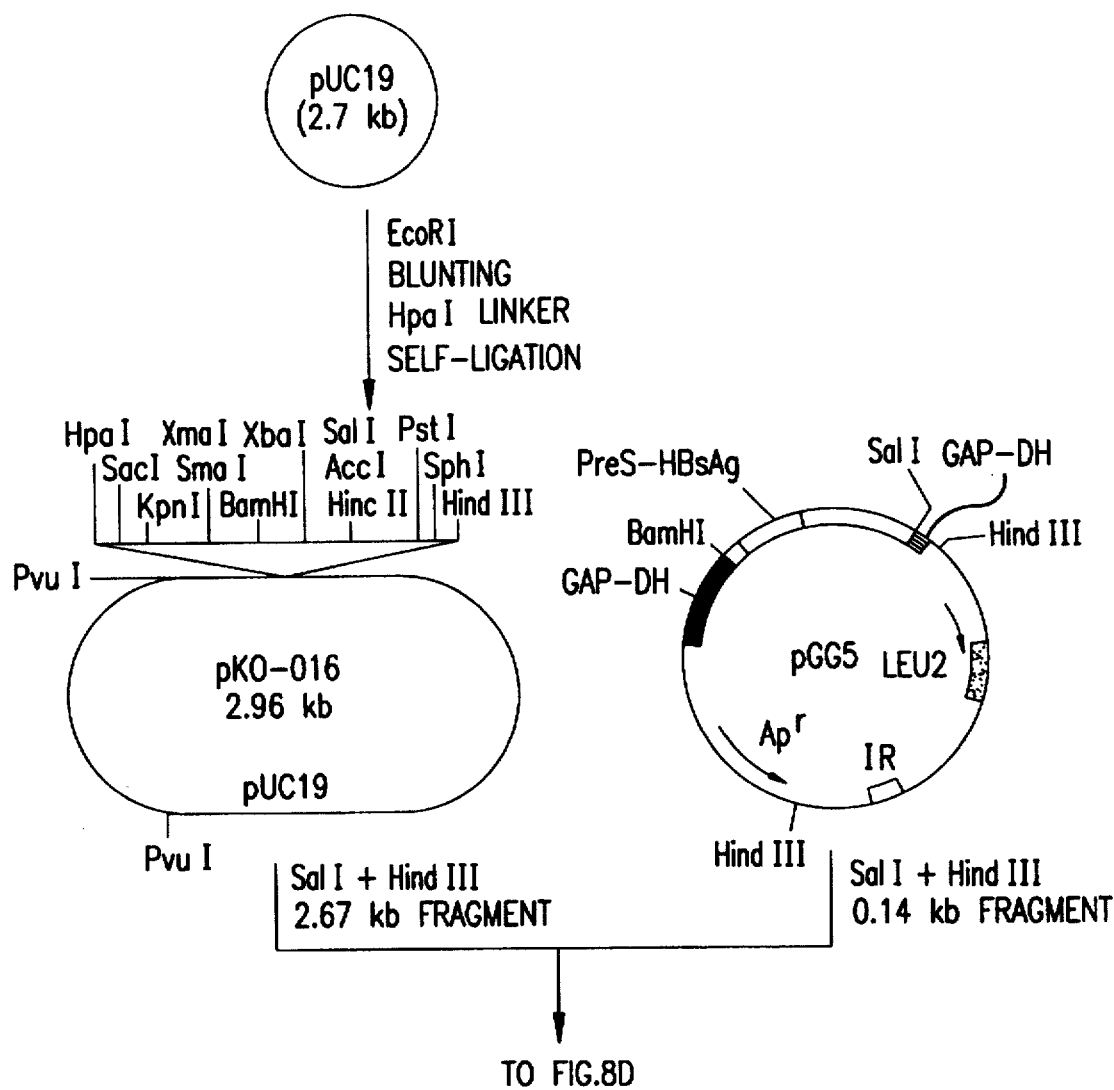
Figure 8E:
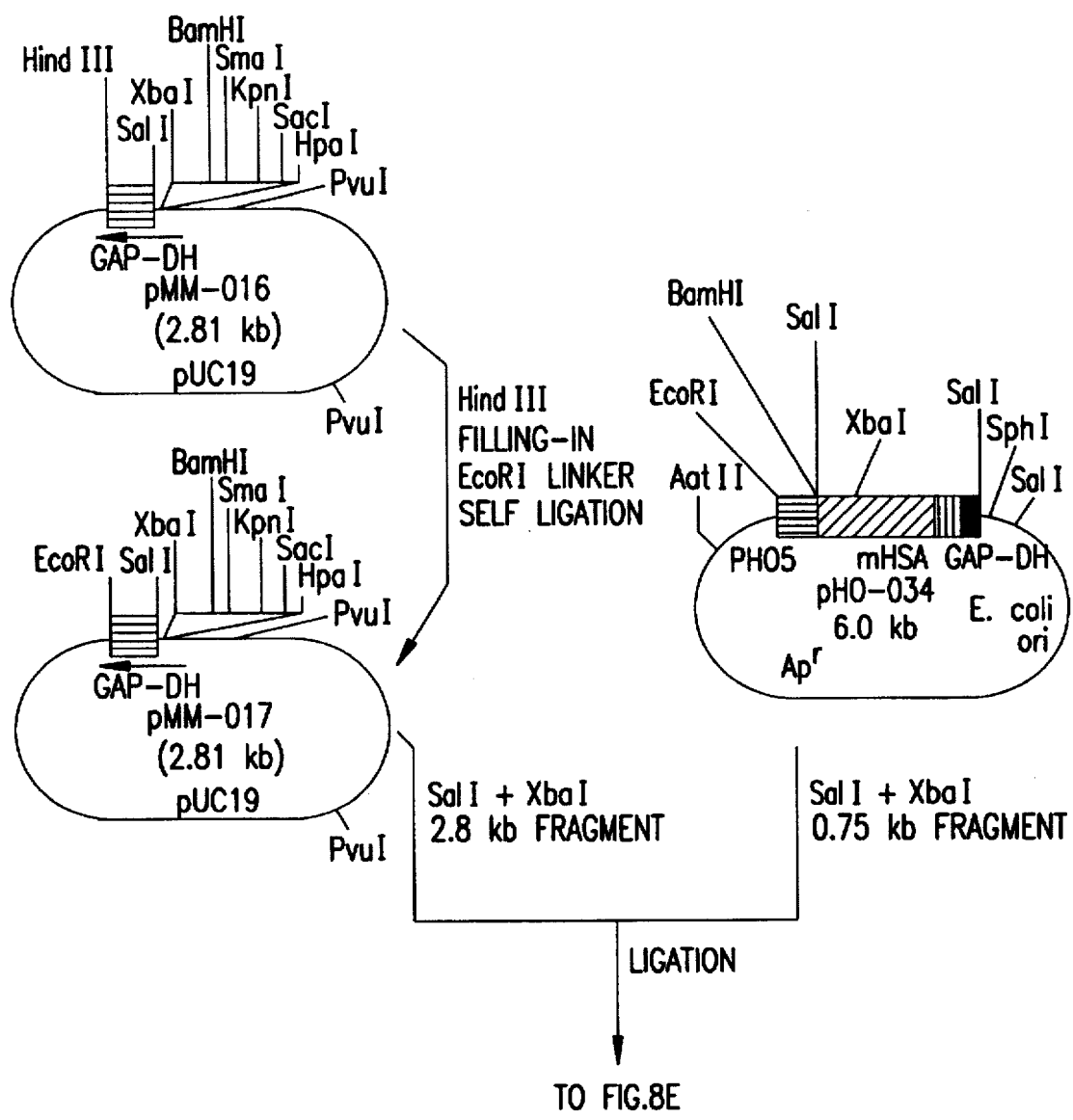
Figure 8F:
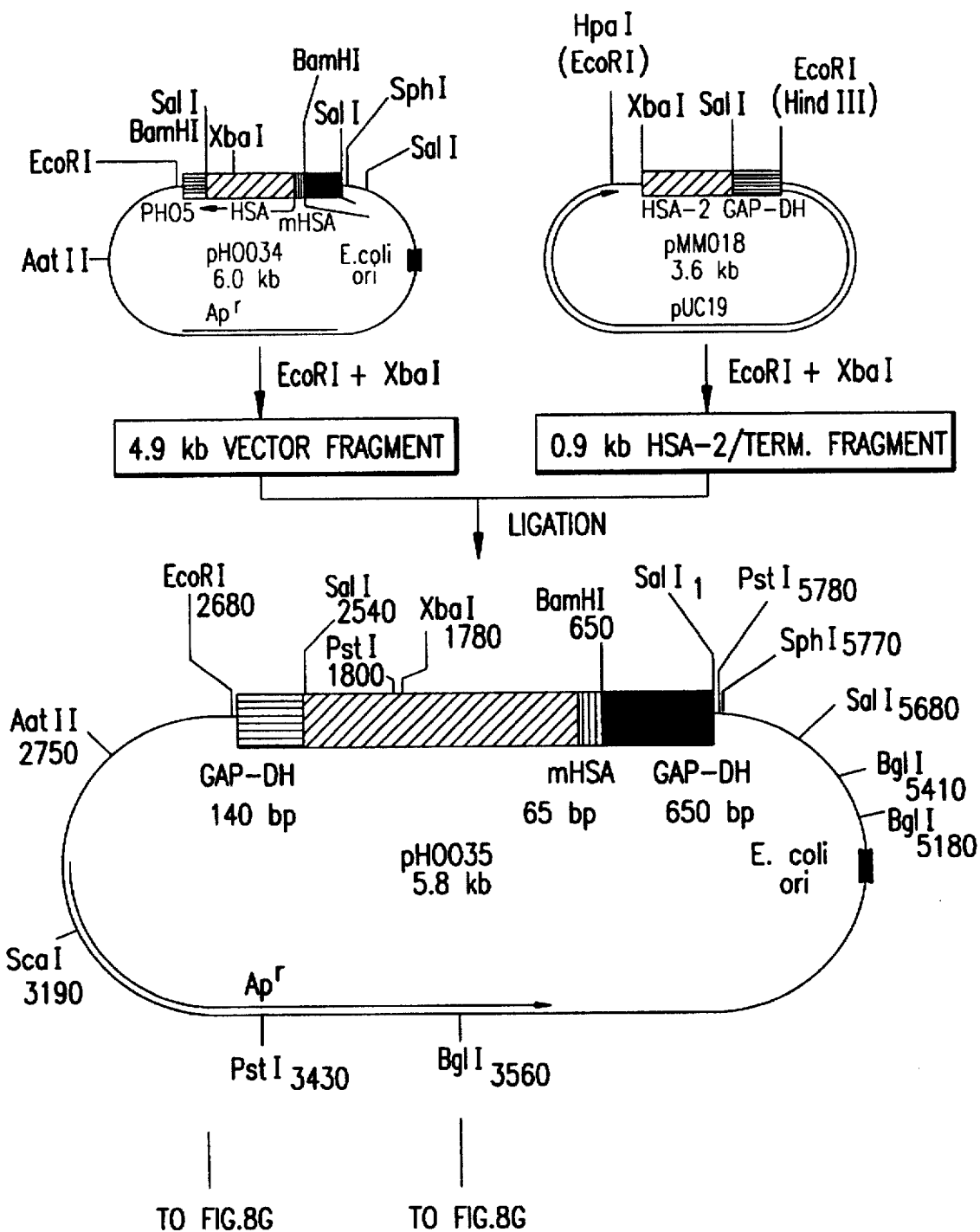
Figure 8G:
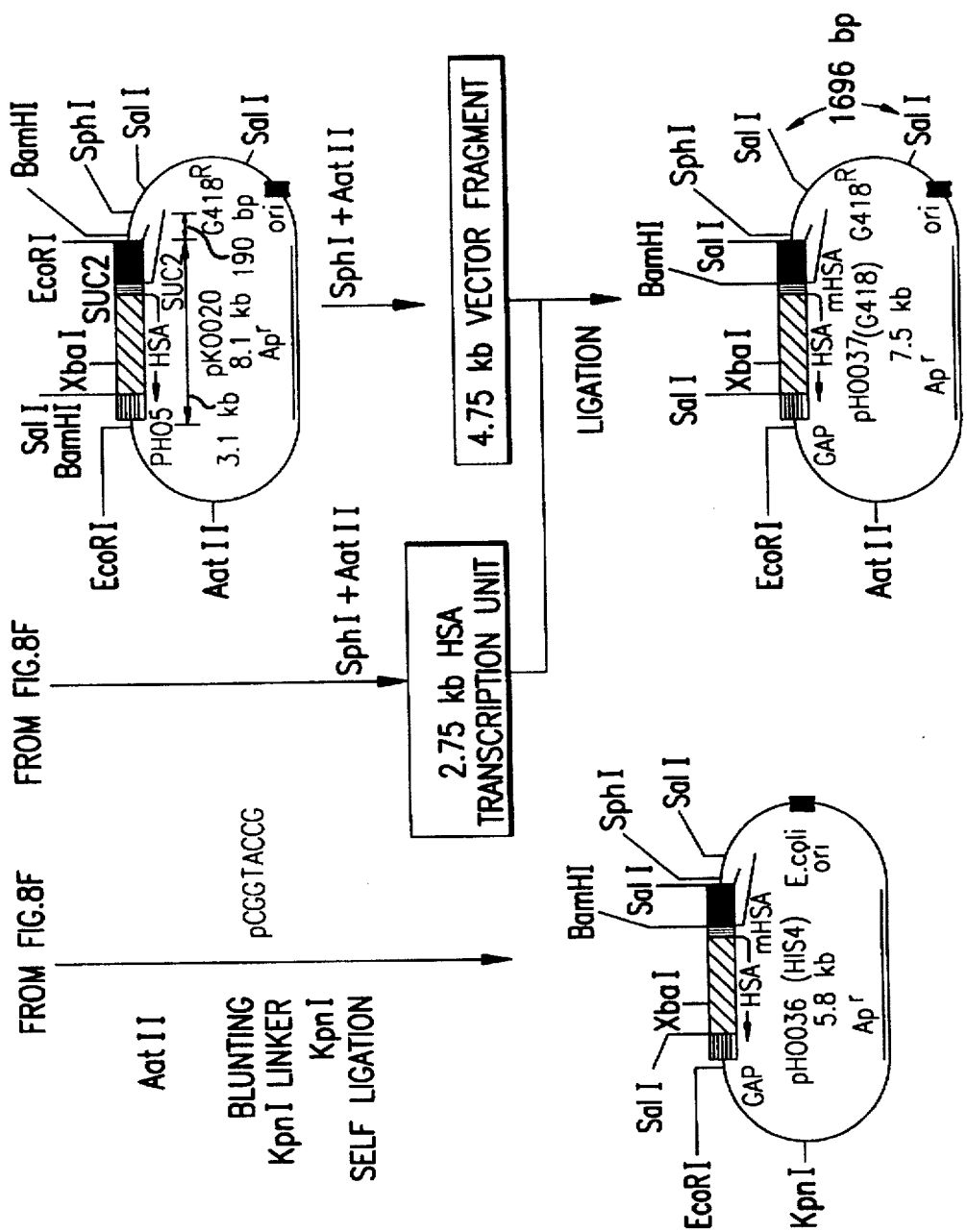
Figure 8H:
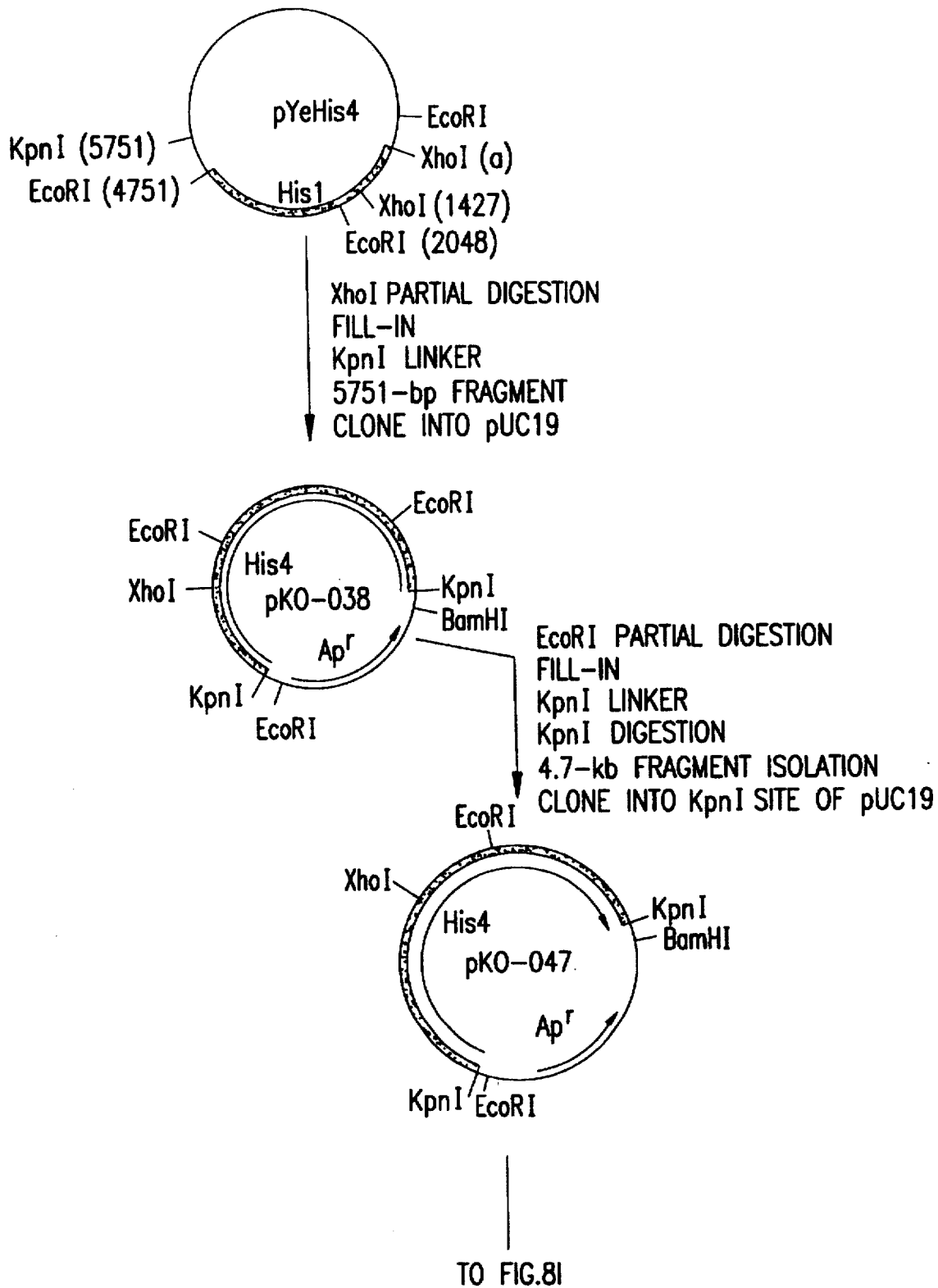
Figure 8I:
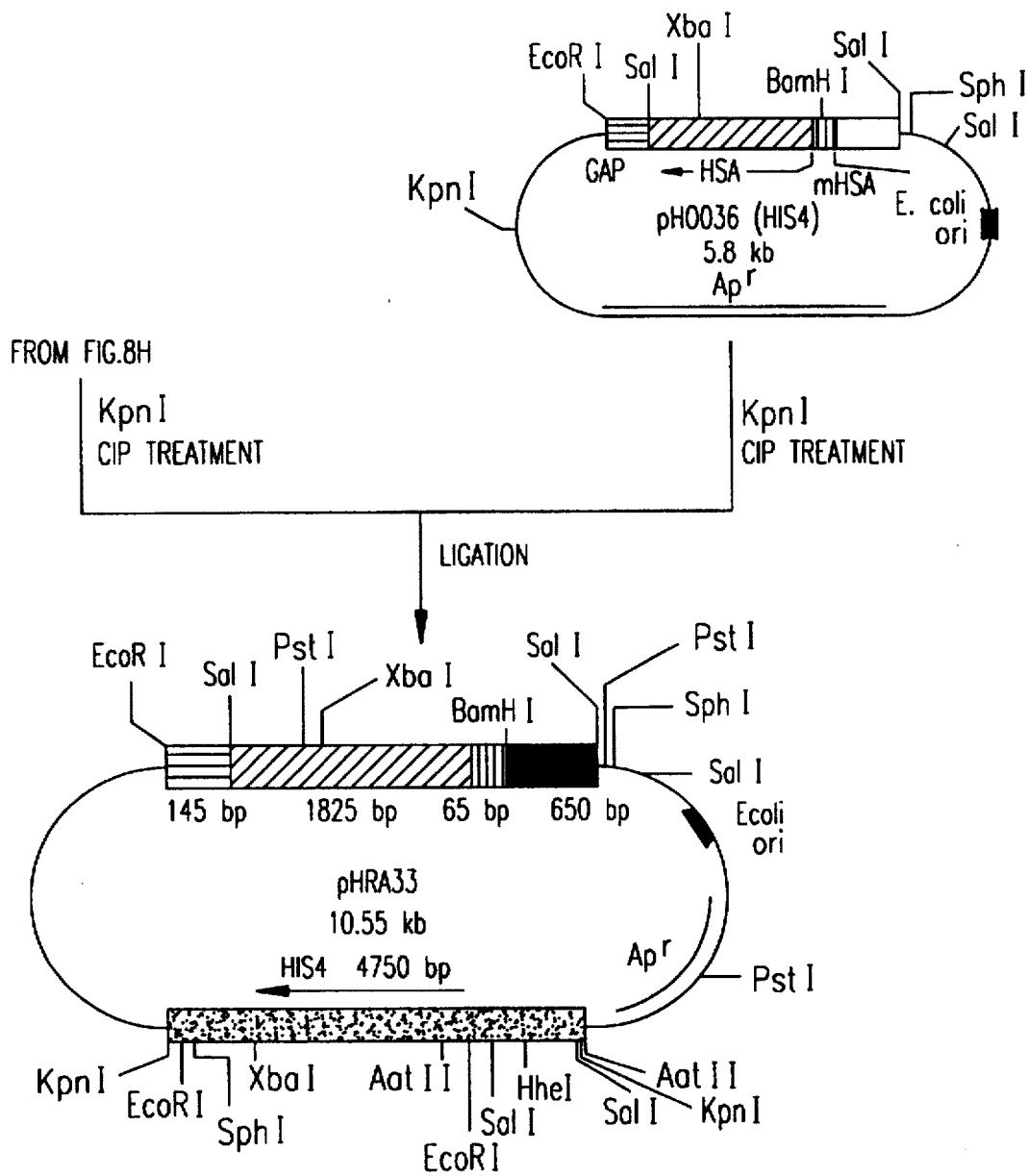
Figure 9:
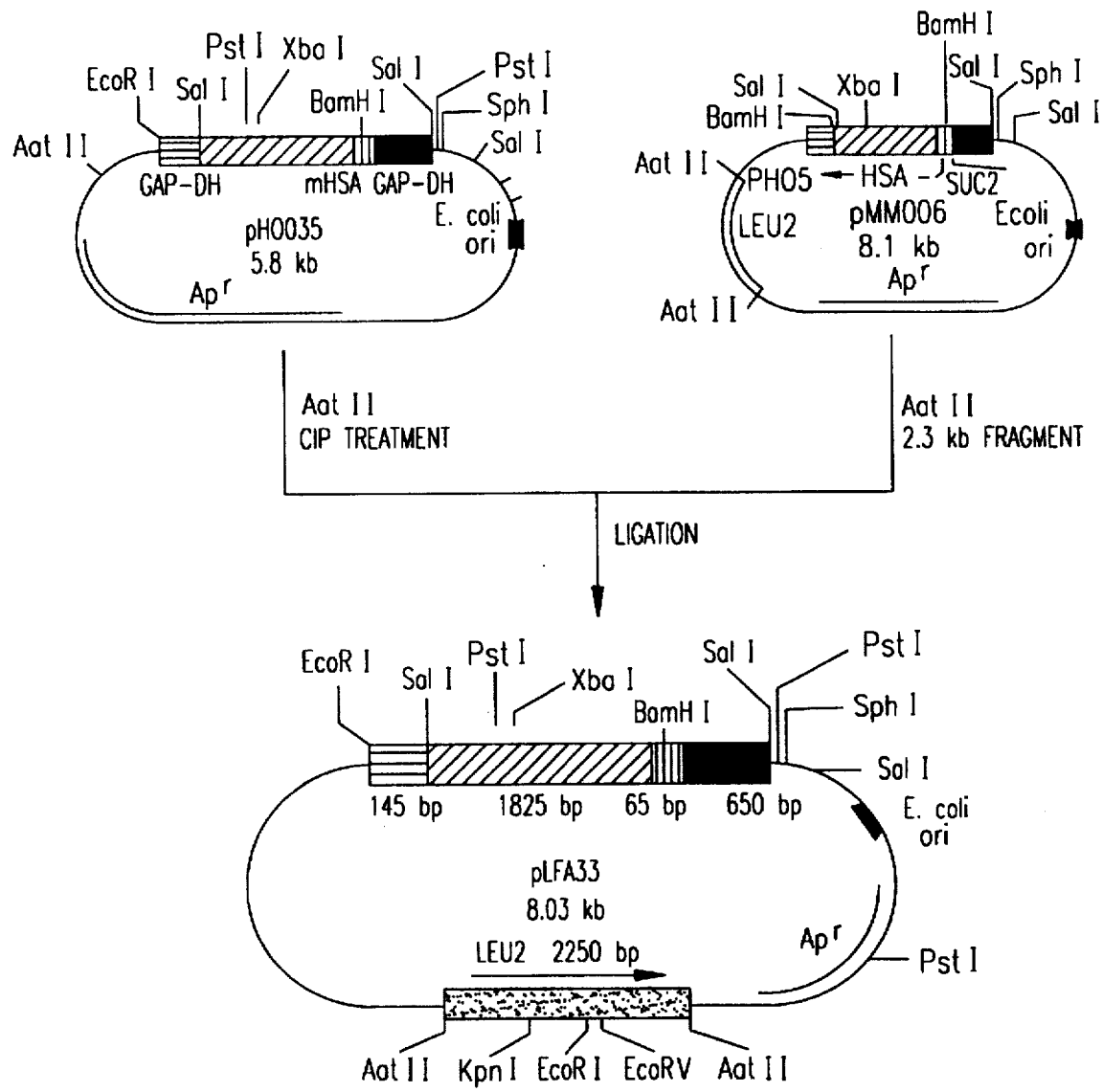
FIG. 9 shows a process for constructing the plasmid pLFA33.
Figure 10:
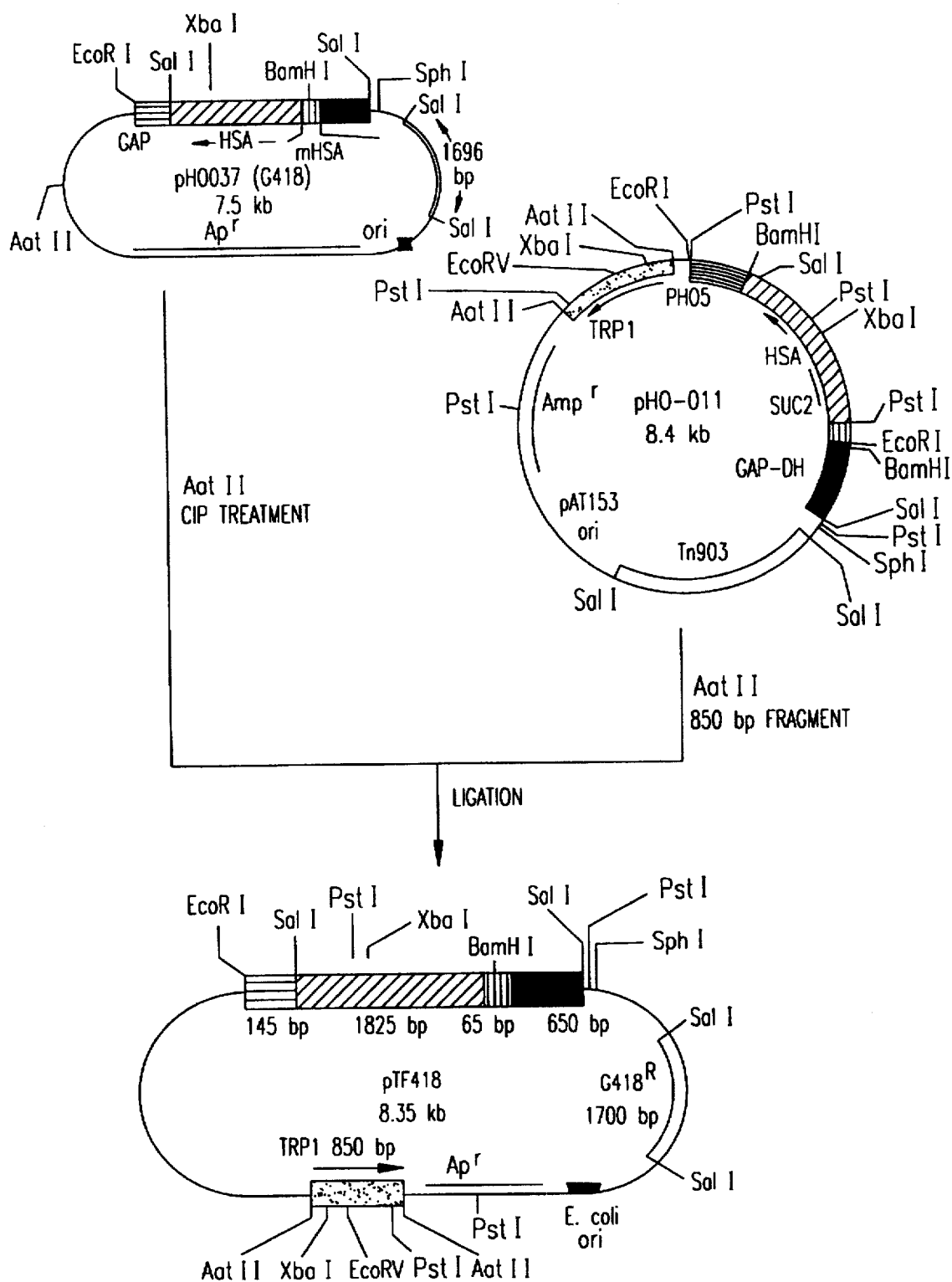
FIG. 10 shows a process for constructing the plasmid pTF418.

7. Construction of plasmid pHO-011 (cf. FIG. 6A–6C)

Plasmid pKM-007 was digested with XbaI and SphI and the 1.7 kb DNA fragment was isolated. Separately, plasmid pKO-020 was digested with XbaI and SphI and the resulting DNA fragment (5.9 kb) was ligated with the above 1.7 kb DNA fragment. Then, the ligation product (pKH010) was digested with AatII, followed by treatment with CIP.

Plasmid pBTI-10 was digested with EcoRI and the 1.45 kb DNA fragment was obtained. Separately, pUC19 was digested with EcoRI and the resulting DNA fragment was treated with CIP. This was ligated with the above 1.45 kb DNA fragment to obtain plasmid pHO003. This plasmid was digested with EcoRI and BRIII and the cohesive ends of the thus-obtained 0.85 kb DNA fragment were made blunt, followed by ligation with the AatII linker. This ligation product was ligated with the above-obtained pKH010-derived DNA fragment and plasmid pHO-011 was obtained.

The plasmid pHO-011 contains the coding region of the TRP1 gene as the sequence homologous to a part of the host yeast cell chromosomal sequence. In this plasmid, the SUC2 signal sequence, the structural gene for HSA and the PHO5 terminator are joined together under the control of the GAP-DH promoter. This plasmid contains the G418 resistance gene as a selective marker gene to serve in yeasts.

The plasmids pMM-006, pMS-008 and pHO-011 have been deposited with the Fermentation Research Institute, Agency of Industrial Science and Technology, Ministry of International Trade and Industry since Apr. 28, 1989 under the Budapest Treaty, as follows:

(1) Name of microorganism: pMM006/E. coli JM109
    Deposit number: FERM BP-2404
(2) Name of microorganism: pMS008/E. coli JM109
    Deposit number: FERM BP-2406
(3) Name of microorganism: pHO011/E. coli HB101
    Deposit number: FERM BP-2405

[III] Transformation of *Saccharomyces cerevisiae* AH22 with plasmid pMM-006

*Saccharomyces cerevisiae* AH22 was used as the host.

The strain *Saccharomyces cerevisiae* AH22 is of the mating type "a" and has mutations in the histidine synthesis gene (his4) and leucine synthesis gene (leu2). Therefore, it cannot proliferate unless histidine and leucine are added to the culture medium.

The plasmid pMM-006 for secretory HSA expression was introduced into the chromosome of the yeast strain *Saccharomyces cerevisiae* AH22 in the following manner.

*Saccharomyces cerevisiae* AH22 was shake-cultured for 16 hours in 50 ml of YPD medium (prepared by dissolving 10 g of yeast extract and 20 g of Bacto-peptone in water, making the solution 900 ml, autoclaving and admixing with 100 ml of separately autoclaved 20% glucose) at 37° C. Cells were harvested by centrifugation, suspended in 20 ml of water and then recovered by centrifugation. The cells were suspended in 10 ml of a solution (pH 8.5) containing 50 mM dithiothreitol, 1.2M sorbitol and 25 mM EDTA and the suspension was shaken gently at 30° C. for 10 minutes. Cells were collected by centrifugation, suspended in 10 ml of 1.2M sorbitol and then recovered by centrifugation. The cells were suspended in 10 ml. of 1.2M sorbitol, then recovered by centrifugation, and suspended in 10 ml of 10 mM EDTA-0.1M sodium citrate (pH 5.8) containing 0.2 mg/ml zymolyase 100T (Kirin Brewery Co.) and 1.2M sorbitol. The suspension was shaken gently at 30° C. for 1 hour. Cells were collected by centrifugation, washed with 10 ml each of 1.2M sorbitol, 10 mM calcium chloride and 1.2M sorbitol in that order. The cells recovered by centrifugation were suspended in 1 ml of 10 mM calcium chloride-1.2M sorbitol. A 100μl portion of the suspension was placed in a sterilized test tube, 5 μl (5 μg) of pMM-006 (linearized by digestion at the unique KpnI site on the LEU2 gene) was added thereto, and the mixture was allowed to stand at room temperature for 15 minutes. Then, 1.2 ml of 10 mM Tris-hydrochloride (pH 7.5) containing 20% polyethylene glycol 4000 and 10 mM calcium chloride was added and, after gentle shaking, the mixture was allowed to stand at room temperature for 20 minutes. Cells were collected by centrifugation and suspended in 0.1 ml of YPD medium containing 1.2M sorbitol and 10 mM calcium chloride. The mixture was shaken gently at 30° C. for 30 minutes. A 1.5-, 10-, 20- or 50-μl portion of the suspension was mixed with agar medium and the mixture was spread on a 10-ml leucine-free medium plate maintained at 45° C. After solidification of the whole plate, stationary culture was conducted at 30° C. for 3 days. Colonies formed were collected using a toothpick and suspended in 3 ml of a medium composed of 0.7% yeast. nitrogen base and 2% glucose and shake-cultured at 30° C. for 2 days. A 1.5-ml portion of the culture was centrifuged, the cells collected were suspended in 3 ml of YPD medium (prepared by dissolving 10 g of yeast extract and 20 g of Bacto-peptone in water, making the solution 900 ml, autoclaving and mixing with 100 ml of separately autoclaved 20% dextrose), and shake culture was conducted a 30° C. The culture supernatant was assayed for HSA concentration at intervals by the RPHA method. On the third day, the HSA concentration attained a maximum of 40 μg/ml.

The thus-obtained transformant was named TMM-21-17.

[IV] Screening of transformant TMM-21-17 (stability of LEU2gene and yield of HSA)

(1) The site of integration of the HSA gene in TMM-21-17 was determined using the technique of Southern blotting and it was confirmed that the gene had actually been integrated into the LEU2region on the chromosome.

(2) The stability of the HSA gene integrated was estimated with the yield of HSA and the absence of leucine requirement as indices. Even after about 60 generations of subcultivation in a nonselective medium, the HSA gene retention was 100%.

[V] Transformation of transformant TMM-21-17 with plasmid pMS-008

The same method as described above in section [III] was used except for the following:

Host: Transformant TMM-21-17;

Plasmid: pMS-008;

State of plasmid introduced: Linearized by digestion at the unique NheI site on the HIS4gene in pMS-008;

Transformation medium: Yeast nitrogen base without amino acids was used in lieu of yeast nitrogen base (as a result, the medium was leucine- and histidine-free).

Human serum albumin yield: 70 μg/ml.

The thus-obtained transformant was named TMS-31-3-7.

[VI] Screening of transformant TMS-31-3-7

The same method as described above in section [IV] was used.

(1) The sites of integration of the HSA gene were examined by Southern blotting. It was confirmed that the gene had actually been integrated into the LEU2region and HIS4region on the chromosome.

(2) The stability of the HSA gene was estimated with the yield of HSA and the absence of histidine requirement as indices. Even after about 60 generations of subcultivation in a nonselective medium, the HSA gene retention was 100%.

[VII] Transformation of transformant TMS-31-3-7 with plasmid pHO-011

The same method as described above in section [III] was used except for the following;

Host: Transformant TMS-31-3-7;

Plasmid: pHO-011;

State of plasmid introduced: Linearized by digestion at the unique EcoRV site on the TRP1 gene in pHO-011;

Transformation medium: A protoplast preparation for transformation was suspended in YPD medium supplemented with 1.2M sorbitol, 3% noble agar and 0.2% monopotassium phosphate;

Plate: YPD medium supplemented with 1.2M sorbitol, 3% noble agar and 100 μg/ml of G418;

Human serum albumin yield: 80 μg/ml.

The thus-obtained transformant was named TMS-32.

[VIII] Screening of transformant TMS-32

The same method as described above in section [IV] was used.

(1) The sites of integration of the HSA gene were investigated by the technique of Southern blotting. It was confirmed that the gene had actually been integrated into the LEU2, HIS4 and TRP1 regions on the chromosome.

(2) The stability of the HSA gene was estimated with the yield of HSA and the resistance to G418 as indices. Even after about 60 generations of subcultivation in a nonselective medium, the HSA gene retention was 100%.

It was thus confirmed that, in the transformant TMS-32, the HSA gene was integrated into the chromosome of the host yeast Saccharomyces cerevisiae AH22 at three sites, namely the LEU2, HIS4 and TRP1 regions.

As described hereinabove in detail, the present invention produces the following effects; The desired gene, namely the HSA gene, can hardly be lost from the host cell and can be retained therein without application of any selection pressure and, furthermore, the expression of HSA can be increased by integrating the desired gene into a plurality of sites.

EXAMPLE 2

Saccharomyces cerivisiae AH22 was used as the host and an HSA-producing multiple integrant strain, A124, was produced.

[I] Incorporation of HSA transcription unit into Strain AH22

An integration vector containing the HSA transcription unit composed of GAP-DH promoter/mHSA signal HSA cDNA/GAP-DH terminator was incorporated into the TRP1 region of Saccharomyces cerivisiae AH22 and 34 HSA-producing integrant (AI) clones were obtained. Among them, two clones showing a good growth, namely AI-13 capable of producing 50 mg/l HSA and As-32 capable of producing 40 mg/l of HSA, were screened out and used as candidate strains for multiple integration.

A. Materials and methods (a) Strain

Saccharomyces cerivisiae AH22 (a, LEU2, HIS4, CAN1) was used.

(b) The integration vector pTF418 (FIGS. 2A–2B) was used. pTF418 is an integration vector containing the HSA transcription unit composed of GAP-DH promoter/mHSA singal/HSA cDNA/GAP-DH terminator. It contains the TRP1 gene as a sequence homologous to the corresponding portion of the yeast host cell chromosome sequence. It also contains the G418 resistance gene as a yeast selection marker gene. In this vector, the direction of TRP1 transcription is the same as that of HSA transcription. The GAP-DH terminator used was that described in JP-A-62-175180 and the mHSA signal sequence employed was that described in EP-A-319641.

pTF418 was digested with the restriction enzyme EcoRV capable of cleaving pTF418 only at a single site in the TRP1 region, and the concentration was adjusted to 0.5 The resctriction enzyme analysis data for pTF418 are shown below in Table 1.

TABLE 1

| Restriction enzyme | Sizes of resulting fragments (kb) | Remarks |
|---|---|---|
| SalI | 4.1, 2.5, 1.7, 0 | 1.7: Tn903 |
| SalI/BamHI | 4.1, 1.9, 1.7, 0.65, 0.09 | |
| XbaI | 7.2, 1.2 | Confirmation of directionality |
| XbaI/EcoRI | 7.2, 0.95, 0.25 | |
| AatII | 7.5, 0.85 | 0.85: TRP1 frag. |
| PstI | 4.1, 1.8, 1.8, 0.7 | |
| EcoRI | 8.4 | |
| EcoRV | 8.4 | Site only in TRP1 |
| EcoRI/EcoRV | 7.9, 0.5 | |

(c) Transformation of *S. cerevisiae* AH22 with plasmid pTF418

The same method as described above in Example 1, [III] was used except for the following Plasmid: pTF418

State of plasmid introduced: pTF418 was linearized by cleavage at the unique EcoRV site on the TRP1 gene. Transformation medium: A protoplast preparation for transformation was suspended in YPD mediumn supplemented with 1.2M sorbitorl, 3% noble agar amd 0.2% potassium phosphate. For plate preparation, YPD medium supplemented with 1.2M sorbitol, 3% noble agar and 100 µg/ml G-418 was used.

(d) Integrant recovery

Of the colonies that had appeared on the regeneration plate, 36 colonies were each collected with a toothpick, suspended in sterilized water and isolated as single colony on a YPD gen$_{100}$ plate (YPD plate containing 100 µg/µl). For each colony, a clone was optionally selected as an integrant with the vector incorporated in the TRP1 region of the chromosome (as confirmed by the Southern blotting technique).

(e) Cultivation of integrants

1) Culture in medium-sized test tubes: A loopful of cells were collected from the YPD gen$_{100}$ plate and cultivated in 3 ml of YPD medium placed in a medium-sized test tube at 30° C. and 140 rpm for 72 hours.

2) Culture in flasks: A loopful of cells were collected from the YPD gen$_{100}$ plate and cultivated in 3 ml of YPD medium in a medium-size test tube at 30° C. and 140 rpm for 24 hours and the culture was used for inoculation of 50 ml of YPD placed in a 300-ml flask at an initial cell concentration corresponding to A$_{540}$ nm=0.3. Flask culture was carried out at 30° C. and 140 rpm for 72 hours.

(f) Proliferation rate and HSA yeild determinations

Each culture obtained in the above manner was sampled and checked for cell proliferation rate in terms of A$_{540}$ nm and for HSA yield by the RPHA method.

(g) Stability in subculturing

Subculture was repeated seven times on a YPD plate (nonselective plate) and, furthermore, colonies were isolated each as a single colony on a YPD plate. Ten clones optionally selected were each inoculated onto a YPD plate (nonselective plate) and a YPD gen$_{100}$ plate (G418 selective plate) and judged as to whether they retained the G418 gene.

The stability in subculturing was further evaluated in terms of HSA yield. A loopful of cells were collected from each of the initial selective plate (subculture 0) and the 7th subculture plate and cultured in 3 ml of YPD medium in a medium-sized test tube at 30° C. and 140 rpm for 90 hours. Each culture was sampled and checked for cell proliferation rate (in terms of A$_{540}$ nm) and for HSA yield (by the RPHA methods).

(h) Integrant preservation

A loopful of cells were collected from the selective plate, inoculated into 50 ml of YPD medium in a 300-ml flask and cultivated at 30° C. and 140 rpm for 24 hours. Cells were harvested by centrifugation (2,500 rpm, 10 minutes) and suspended in 15% glycerol-YPD medium in a concentration corresponding to A$_{540}$ nm=100. The suspension was distributed in 1-ml portions into tubes and stored frozen at −80° C.

B. Results (a) Transformation efficiency

The number of transformant colonies per microgram (µg) of the vector was about 500. This value was sufficient for screening out high-productivity HSA producer integrants.

(b) Primary screening of high productivity HSA producer integrants (culture in medium-sized test tubes)

The 34 Al-derived clones (Al-1 to 34) isolated were cultured in medium-sized test tubes and, after 72 hours of cultivation, evaluated for proliferation rate and HSA yield. Two clones, Al-13 and Al-29, showed an HSA yield of 60 mg/l and eight clones showed an HSA yield of 40 mg/l. The two clones showing an HSA yield of 60 mg/l and two more clones selected from the proliferation viewpoint, Al-25 and Al-32, were subjected to secondary screening.

(c) Secondary screening of high-productivity HSA producer integrants (culture in flasks)

The above-mentioned four clonal strains were cultured in flasks and, after 24, 48 and 72 hours of cultivation, evaluated for proliferation rate and HSA yield.

After 72 hours of cultivation, Al-29 showed an HSA yield of 60 mg/l, Al-13 and HSA yield of 50 mg/l, and Al-25 and Al-32 an HSA yield of 40 mg/l.

Al-29 was inferior in growth rate to the other strains.

(d) Stability in subculturing

The stability in subculturing was estimated after seven subcultures on the nonselective plate with the retention of the G418 gene as an index. The stability of Al-25 was 90% while the other clones showed a stability of 100%. Each clone showed no decrease in HSA yield.

[III Production of HSA-producing multiple integrant Al2 strains

The strains Al-13 and Al-32 produced by incorporation of the integration vector containing the HSA transcription unit composed of GAP-DH promoter/mHSA signal/HSA cDNA/ GAP-DH terminator into the TRP1 region of the chromosome of the strain AH22 were used as the hosts and multiple integrant Al2 strains with another integration vector containing the above-mentioned transcription unit being incorporated in the LEU2region thereof were obtained. Among them, a strain, Al2-2Y, showing good proliferation and an HSA yield of 80 mg/l was screened out and used as a candidate for further multiple integration.

A. Materials and methods (a) Strain

The strains Al-13 and Al-32 derived from the strain AH22 by incorporation of pTF418 into the TRP1 region were used.

(b) The integration vector pLFA33 (FIG. 4A–4B) was used. pLAF33 is an integration vector containing the HSA transcription unit composed of GAP-DH promoter/mHSA signal/HSA cDNA/GAP-DH terminator and has a sequence homologous to the corresponding portion of the host yeast cell chromosome and the LEU2gene as a selective marker gene to serve in yeasts. LEU2and HSA are transcribed in the same direction.

pLFA33 was cleaved with KpnI capable of cleaving pLFA33 at one single site in the LEU2region and the concentration was adjusted to 1.5 µg/µl. The restriction enzyme analysis data for pLFA33 were as shown in Table 2.

TABLE 2

| Restriction enzyme | Sizes of resulting fragments (kb) |
|---|---|
| AatII | 2.23, 5.8 |
| EcoRI | 1.37, 6.66 |
| EcoRV | 8.03 |
| KpnI | 8.03 |
| PstI | 1.82, 2.35, 3.86 |
| SalI | 0.12, 2.54, 5.37 |
| SphI | 8.03 |
| XhaI | 8.03 |
| BamHI/SalI | 0.12, 0.65, 1.89, 5.37 |
| KpnI/XbaI | 1.88, 6.15 |

(c) Transformation of Al-13 strain with plasmid pLF-A33

The same method as described above in Example 1, [III] was used except for the following Host: Transformant Al-13.

Plasmid: pLF-A33.

State of plasmid introduced: Linearized by digestion with KpnI at the unique KpnI site on the LEU2gene of pLF-A33.

Transformation medium: A protoplast preparation for transformation was suspended in YPD medium supplemented with 0.7% yeast nitrogen base, 1.2M sorbitol, 3% noble agar and 2% glucose. For plate preparation, a leucine-free medium containing 0.7% yeast nitrogen base, 1.2M sorbitol, 3% noble agar and 2% glucose was used.

(d) integrant recovery

Of the colonies that had appeared on the regeneration plate, 36 colonies were each collected with a toothpick, suspended in sterilized water and isolated as a single colony on a YPD plate. For each colony, a clone was optionally selected as an integrant with the vector incorporated in the LEU2region of the chromosome (as confirmed by the Southern blotting technique).

(e) Cultivation of integrants

1) Culture in medium-sized test tubes

A loopful of cells were collected from a YNB plate (0.7% yeast nitrogen base, 2% dextrose, 1.5% agar) and cultivated in 3 ml of YPD medium in a medium-sized test tube at 30° C. and 140 rpm for 72 hours.

2) Culture in flasks

A loopful of cells were collected from the YNB plate and cultivated in 3-ml of YPD medium in a medium-sized test tube at 30° C. and 140 rpm for 24 hours and the culture was used for inoculation of 50 ml of YPD medium in a 300-ml flask at an initial cell concentration corresponding to $A_{540}$ nm=0.2. Flask culture was carried out at 30° C. and 140 rpm for 72 hours.

(f) Proliferation rate and HSA yield determinations

Each culture obtained in the above manner was samples and checked for cell proliferation rate in terms of $A_{540}$ nm and of HSA yield by the RPHA method.

(g) Stability in subculturing

Subculture was repeated six times on a YPD plate (nonselective plate) and, furthermore, colonies were isolated each as a single colony on a YPD plate. Ten clones optionally selected were each inoculated onto a YPD plate (nonselective plate), a YPD gen$_{100}$ plate (G418 selective plate) a YNB plate (LEU selective plate) and judged as to whether the G418 gene or LEU2gene was retained therein.

(h) Integrant preservation

A loopful of cells were collected from the selective plate and cultured in 3 ml of YPD medium in a medium-sized test tube at 30° C. and 140 rpm for 24 hours. The culture was used to inoculate 50 ml of YPD medium in a 300 ml flask and cultivation was carried out at 30° C. and 140 rpm for further 24 hours. Cells were harvested by centrifugation (2,500 rpm, 10 minutes) and suspended in 15% glycerol-YPD medium at a concentration corresponding to $A_{540}$ nm=100. The suspension was distributed in 1.5 ml portions into tubes and stored frozen at −80° C.

B. Results

Al-13-derived Al2 transformants were give Al2-Y series codes, and Al-32-derived Al2 transformants Al2-Z series codes.

(a) Transformation efficiency

For both Al-13 and Al-32 used as the hosts, the number of transformant colonies found per microgram (μg) of the vector was about 30.

(b) Primary screening of high-productivity HSA producer integrants (culture in medium-sized test tubes)

The 30 Al2-derived clones (Al2-1Y to 15Y, Al2-1Z to 15Z) and the two Al2 transformants used as the hosts, namely Al-13 and Al-32, were cultured in medium-sized test tubes and, after 72 hours of cultivation, evaluated for proliferation rate and HSA yield. While the host Al-13 showed an HSA yield of not less than 40 mg/l and the host Al-32 showed an HSA yield of 40 mg/l, 5 clones belonging to the Al-12-Y series and 3 clones belonging to the Al-12-Z series showed an HSA yield of not less than 60 mg/l. Among these, Al2-2Y, Al2-10Y and Al2-11Z apparently capable of giving a relatively high yield of HSA were selected and subjected to secondary screening.

(c) Secondary screening of high-productivity HSA producer integrants (culture in flasks)

Each of the above three strains was cultured in a flask and, after 24, 48 and 72 hours of cultivation, evaluated for proliferation rate and HSA yield.

While the HSA yield after 72 hours of cultivation was 60 mg/l with the host Al-13 and 40 mg/l with the host Al-32, the three strains Al2-2Y, Al2-10Y and Al2-11Z all showed an HSA yield of 80 mg/l after 72 hours of cultivation.

The three transformants showed no change in proliferation rate as compared with the hosts.

(d) Stability in subculturing

For each of the three strains, the stability in subculturing as evaluated using, as an index, the retention of the G418 gene after six repetitions of subculture on a nonselective plate was 100% and the stability in subculturing as evaluated using the retention of the LEU2gene as an index was also 100%.

[III] Production of HSA-producing multiple integrant Al24

The Al2-2Y strain with the two integration vectors each containing the HSA transcription unit composed of GAP-DH promoter/mHSA signal/HSA cDNA/GAP-DH terminator being incorporated in the TRP1 region and LEU2region, respectively, on the chromosome of the A22 strain was used as the host and multiple integrant Al24 strains with a third integration vector containing the above-mentioned transcription unit being further incorporated in the HIS4 region were produced. Among them, a strain, Al24-35, which was superior in HSA yield, ability to proliferate and marker gene stability was selected as a strain for large-scale culture.

A. Materials and methods (a) Strain

The strain Al2-2Y produced by incorporation of pTF418 and pLFA33 into the TRP1 region and LEU2region, respectively, of the strain AH22 was used.

(b) The integration vector pHRA33 (FIG. 5) was used.

pHRA33 is an integration vector containing the HSA transcription unit composed of GAP-DH promoter/mHSA signal/HSA cDNA/GAP-DH terminator and has a sequence homologous to the corresponding portion of the host yeast cell chromosome sequence and, as a yeast selective marker gene, the HIS4gene. HIS4and HSA are transcribed in the reverse direction.

For incorporation, pHRA33 was digested with NheI, which cleaved pHRA33 at one single site in the HIS4 region, and the concentration was adjusted to 1.0 µg/µl. The results of analysis of pHHRA33 with restriction enzymes are shown in Table 3.

TABLE 3

| Restriction enzyme | Sizes of resulting fragments (kb) |
|---|---|
| AatII | 2.29, 8.26 |
| BamHI/SalI | 0.12, 0.65, 1.57, 1.89, 3.16, 3.16 |
| EcoRI | 0.07, 2.7, 7.78 |
| KpnI | 4.75, 5.8 |
| NheI | 10.55 |
| PmaCI | 10.55 |
| PstI | 1.82, 2.35, 6.38 |
| SalI | 0.12, 1.57, 2.54, 3.16, 3.16 |
| SphI | 2.99, 7.56 |
| XbaI | 2.06, 8.49 |
| XhoI | 1.43, 9.12 |

(c) Transformation of A12-2Y with plasmid pHRA33 The same method as described above in Example 1, (III) was used except for the following:

Host: Transformant A12-2Y.
Plasmid: pHRA33.
State of plasmid introduced: Linearized for introduction by digestion (cleavage) at the unique site NheI on the HIS4gene of pHRA33.
Transformation medium: A protoplast preparation for transformation was suspended in YPD medium supplemented with 0.7% yeast nitrogen base without amino acids, 1.2M sorbitol, 3% noble agar and 2% glucose. For plate preparation, a leucine- and histidine-free medium containing 0.7% yeast nitrogen base without amino acids, 1.2M sorbitol, 3% noble agar and 2% glucose.

(d) Integrant recovery

Of the colonies that had appeared on the regeneration plate, 42 colonies were each collected with a toothpick, suspended in sterilized water and isolated as a single colony on a YPD plate. For each colony, a clone was optionally selected as an integrant with the vector incorporated in the HIS4region of the chromosome (as confirmed by the Southern blotting technique) after confirmation of the fact that it could grow in a YNB w/o a.a. plate (0.7% yeast nitrogen base without amino acids, 2% dextrose, 1.5% agar).

(e) Cultivation of integrants

1) Culture in medium-sized test tubes

A loopful of cells were collected from the YNB w/o a.a. plate and cultivated in 3 ml of YPD medium in a medium-sized test tube at 30° C. and 140 rpm for 72 hours.

2) Culture in flasks

A loopful of cells were collected from the YNB w/o a.a. plate and cultivated in 3 ml of YPD medium in a medium-sized test tube at 30° C. and 140 rpm for 24 hours, and the culture was used to inoculate 50 ml of YPD medium or glucose-ammonium acetate medium in a 300 ml flask at an initial cell concentration corresponding to $A_{540}$ nm=0.2. Flask culture was conducted at 30° C. and 140 rpm for 72 hours.

(f) Proliferation rate and HSA yield determinations

Each culture obtained in the above manner was sampled and checked for cell proliferation rate (in terms of $A_{540}$ nm) and for HSA yield by the RPHA method)

(g) Stability in subculturing

Subculture on a YPD plate (nonselective plate) was repeated six times, followed by isolation of each colony as a single colony on a YPD plate. Ten clones optionally selected were each inoculated onto a YPD plate (nonselective plate), YPD gen$_{100}$ plate (TRP selective plate), YNB plate (LEU selective plate) and YNB w/o a.a.+LEU plate (HIS selective plate) for judgment as to whether the G418 gene, LEU gene and HIS4gene were retained therein.

The stability in subculturing was further evaluated in terms of HSA yield. Thus, a loopful of cells were collected from each of the initial selective plate (subculture 0) and the 6th subculture plate and cultured in 3 ml of YPD medium in a medium-sized test tube at 30° C. and 140 rpm for 90 hours. Each culture was sampled and checked for cell proliferation rate and HSA yield.

(h) Integrant preservation

A loopful of cells were collected from the selective plate, inoculated into 5 ml of YPD medium in a medium-sized test tube and cultivated at 30° C. and 140 rpm for 24 hours. Cells were transferred to a 300 ml flask containing 50 ml of YPD medium and cultivation was performed at 30° C. and 140 rpm for further 24 hours. Cells were harvested by centrifugation (2,500 rpm, 10 minutes) and suspended in 15% glycerol-YPD medium at a concentration corresponding to $A_{540}$ nm=100. The suspension was distributed in 1.5 ml portions into tubes and stored frozen at −80° C.

B. Results (a) Transformation efficiency

The number of transformant colonies obtained per microgram (µg) of the vector was about 1,500. This value was sufficient for screening high-productivity HSA producer strains.

(b) Primary screening of A124 clones (culture in medium-sized test tubes)

The forty-two A-124 clones isolated and the host A12 strain, namely A12-2Y, were cultured in medium-sized test tubes and, after 72 hours of cultivation, evaluated for proliferation rate and HSA yield. While the host A12-2Y showed an HSA yield of 60 mg/liter, all the A124 series clones showed an HSA yield of not less than 60 mg/liter, in some instances not less than 80 mg/liter. Among them, A124-12, A124-13, A124-15, A124-24 and A124-35, which seemed to give relatively high HSA yields, were subjected to secondary screening.

(c) Secondary screening of A124 clones (test of stability in subculturing)

After 6 repetitions of subculture on a nonselective plate, the TRP, LEU and HIS genes were retained 100% in the clones except for A124-13 in which the retention of TRP was 90%. No changes were observed in HSA productivity between before and after subculturing. A124-15 and A124-35, which showed 100% gene retention, high HSA yield and good proliferation, were subjected to third screening (flask culture). These two clones were stored frozen.

(d) Tertiary screening of A124 clones (culture in flasks)

A124-15 and A124-35 were cultured in flasks using a natural medium (YPD medium) and a synthetic medium (glucose-ammonium acetate medium) and, after 24, 48 and 70 hours, checked for proliferation rate and HSA yield.

In the natural medium, A124-35 showed a somewhat higher HSA yield than the value 80 mg/l attained with the host A12-2Y. Both the clones were equally comparable in proliferative capacity to the control.

In the synthetic medium, both the clones were equally comparable in HSA yield (15 mg/l) and in proliferative capacity to the contol strain TMS-33-1 h4.

Based on the above results, the strain A124-35 was selected as a strain for large-scale culture.

The transformant A124-35 has been deposited since Jul. 25, 1989, with the Fermentation Research Institute, Agency of Industrial Science and Technology, Ministry of International Trade and Industry under the Budapest Treaty, as follows:

Name of microorganism: *S. cerevisiae* A124-35

Deposit number: FERM BP-2527.

While the invention has been described in detail and with reference to specific embodiments thereof, it will be apparent to one skilled in the art that various changes and modifications can be made therein without departing from the spirit and scope thereof.

What is claimed is:

1. A transformed *Saccharomyces cerevisiae* or *Pichia pastoris* host cell comprising at least two plasmids integrated into at least two sites of the host cell chromosome, wherein at least one of said plasmids is integrated at each of said sites, wherein said plasmids comprise the following elements operably linked in the 5' to 3' direction: (1) a promoter functional in yeast, (2) a signal sequence enabling albumin secretion from said host cell, (3) a mature human serum albumin-encoding nucleic acid sequence, (4) a transcription terminator and (5) a sequence homologous to a part of the host cell sequence sufficient for integration by homologous recombination such that the plasmid is integrated into a host cell chromosome, wherein said host cell chromosomal sequence is a nucleic acid metabolic pathway gene and wherein the plasmid does not contain a yeast autonomous replication sequence or a yeast origin of replication.

2. The transformed host cell of claim 1, wherein each of said plasmids in said host cell further comprises an antibiotic resistance gene.

3. The transformed host cell of claim 1, wherein said host cell is auxotrophic for an amino acid, is auxotrophic for a nucleic acid or is susceptible to an antibiotic.

4. A method of producing human serum albumin which comprises culturing the transformed host cell of claim 1 under conditions suitable to express human serum albumin and recovering the thus-produced albumin.

5. A method of producing the transformed host cell of claim 1 comprising (i) cleaving each plasmid at a restriction enzyme cleavage site in the sequence homologous to a part of the host chromosomal sequence and (ii) sequentially integrating the cleaved plasmids into the respective homologous sites in the host cell chromosome.

* * * * *